(12) United States Patent
Ostrovsky et al.

(10) Patent No.: US 9,301,750 B2
(45) Date of Patent: Apr. 5, 2016

(54) DEVICE AND METHOD FOR DELIVERY OF MESH-BASED DEVICES

(75) Inventors: Isaac Ostrovsky, Wellesley, MA (US); Jozef Slanda, Milford, MA (US); Jianmin Li, Lexington, MA (US); Alfred Intoccia, Nashua, NH (US); Tim Harrah, Cambridge, MA (US); James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1257 days.

(21) Appl. No.: 12/938,553

(22) Filed: Nov. 3, 2010

(65) Prior Publication Data
US 2011/0106108 A1 May 5, 2011

Related U.S. Application Data

(60) Provisional application No. 61/257,616, filed on Nov. 3, 2009.

(51) Int. Cl.
*A61B 17/10* (2006.01)
*A61B 17/06* (2006.01)
*A61B 17/00* (2006.01)

(52) U.S. Cl.
CPC . *A61B 17/06109* (2013.01); *A61B 2017/00349* (2013.01); *A61B 2017/00805* (2013.01)

(58) Field of Classification Search
CPC .............. A61B 17/06109; A61B 2017/00805; A61B 2017/00349
USPC ........................................................ 206/380
See application file for complete search history.

(56) References Cited

U.S. PATENT DOCUMENTS

| | | |
|---|---|---|
| 3,182,662 A | 5/1965 | Shirodkar |
| 3,212,502 A | 10/1965 | Myers |
| 3,311,110 A | 3/1967 | Singerman et al. |
| 3,372,695 A | 3/1968 | Beliveau et al. |
| 3,472,232 A | 10/1969 | Earl |
| 3,565,073 A | 2/1971 | Giesy |
| 3,608,095 A | 9/1971 | Barry |
| 3,704,712 A | 12/1972 | Giesy et al. |
| 3,763,860 A | 10/1973 | Clarke |
| 3,858,783 A | 1/1975 | Kapitanov et al. |

(Continued)

FOREIGN PATENT DOCUMENTS

| | | |
|---|---|---|
| DE | 3223153 C1 | 8/1983 |
| DE | 4220283 A1 | 12/1993 |

(Continued)

OTHER PUBLICATIONS

Final Office Action Response for U.S. Appl. No. 12/579,704, filed Jan. 18, 2013, 8 pages.

(Continued)

*Primary Examiner* — Gregory Anderson
*Assistant Examiner* — Son Dang
(74) *Attorney, Agent, or Firm* — Brake Hughes Bellermann LLP

(57) ABSTRACT

In some embodiments, a stylet includes a proximal end portion, a distal end portion, and a medial portion between the proximal end portion and the distal end portion. The distal end portion of the stylet is configured to be releasably coupled to a first portion of an implant. The medial portion of the stylet has at least one retention member configured to be releasably coupled to a second portion of the implant.

18 Claims, 14 Drawing Sheets

(56) References Cited

U.S. PATENT DOCUMENTS

| | | | | |
|---|---|---|---|---|
| 3,924,633 | A | 12/1975 | Cook et al. | |
| 4,037,603 | A | 7/1977 | Wendorff | |
| 4,128,100 | A | 12/1978 | Wendorff | |
| 4,235,238 | A | 11/1980 | Ogiu et al. | |
| 4,392,495 | A * | 7/1983 | Bayers | 606/148 |
| 4,441,497 | A | 4/1984 | Paudler | |
| 4,509,516 | A * | 4/1985 | Richmond | 606/53 |
| 4,549,545 | A | 10/1985 | Levy | |
| 4,798,193 | A | 1/1989 | Giesy et al. | |
| 4,824,435 | A | 4/1989 | Giesy et al. | |
| 4,872,451 | A | 10/1989 | Moore et al. | |
| 4,946,467 | A | 8/1990 | Ohi et al. | |
| 4,946,468 | A | 8/1990 | Li | |
| 4,976,717 | A * | 12/1990 | Boyle | 606/119 |
| 5,002,550 | A | 3/1991 | Li | |
| 5,013,292 | A | 5/1991 | Lemay | |
| 5,032,508 | A | 7/1991 | Naughton et al. | |
| 5,064,435 | A | 11/1991 | Porter | |
| 5,078,730 | A | 1/1992 | Li et al. | |
| 5,080,667 | A | 1/1992 | Chen et al. | |
| 5,084,058 | A | 1/1992 | Li | |
| 5,087,263 | A | 2/1992 | Li | |
| 5,112,344 | A | 5/1992 | Petros | |
| 5,149,329 | A | 9/1992 | Richardson | |
| 5,152,749 | A | 10/1992 | Giesy et al. | |
| 5,180,385 | A | 1/1993 | Sontag | |
| 5,207,679 | A | 5/1993 | Li | |
| 5,250,033 | A | 10/1993 | Evans et al. | |
| 5,256,150 | A | 10/1993 | Quiachon et al. | |
| 5,281,237 | A | 1/1994 | Gimpelson | |
| 5,312,422 | A | 5/1994 | Trott | |
| 5,334,185 | A | 8/1994 | Giesy et al. | |
| 5,337,736 | A | 8/1994 | Reddy | |
| 5,362,294 | A | 11/1994 | Seitzinger | |
| 5,368,595 | A | 11/1994 | Lewis | |
| 5,368,756 | A | 11/1994 | Vogel et al. | |
| 5,382,257 | A | 1/1995 | Lewis et al. | |
| 5,383,904 | A | 1/1995 | Totakura et al. | |
| 5,395,349 | A | 3/1995 | Quiachon et al. | |
| 5,403,328 | A | 4/1995 | Shallman | |
| 5,439,467 | A | 8/1995 | Benderev et al. | |
| 5,441,508 | A | 8/1995 | Gazielly et al. | |
| 5,450,860 | A | 9/1995 | O'Connor | |
| 5,456,722 | A | 10/1995 | McLeod et al. | |
| 5,505,735 | A | 4/1996 | Li | |
| 5,507,796 | A | 4/1996 | Hasson | |
| 5,520,700 | A | 5/1996 | Beyar et al. | |
| 5,527,342 | A | 6/1996 | Pietrzak et al. | |
| 5,540,703 | A | 7/1996 | Barker, Jr. et al. | |
| 5,571,119 | A * | 11/1996 | Atala | 606/146 |
| 5,582,188 | A | 12/1996 | Benderev et al. | |
| 5,611,515 | A | 3/1997 | Benderev et al. | |
| 5,628,756 | A * | 5/1997 | Barker et al. | 606/139 |
| 5,645,568 | A | 7/1997 | Chervitz et al. | |
| 5,645,589 | A | 7/1997 | Li | |
| 5,683,418 | A | 11/1997 | Luscombe et al. | |
| 5,690,649 | A | 11/1997 | Li | |
| 5,702,215 | A | 12/1997 | Li | |
| 5,741,299 | A | 4/1998 | Rudt | |
| 5,742,943 | A | 4/1998 | Chen | |
| 5,749,884 | A | 5/1998 | Benderev et al. | |
| 5,816,258 | A | 10/1998 | Jervis | |
| 5,836,315 | A | 11/1998 | Benderev et al. | |
| 5,840,011 | A | 11/1998 | Landgrebe et al. | |
| 5,855,549 | A | 1/1999 | Newman | |
| 5,860,425 | A | 1/1999 | Benderev et al. | |
| 5,860,993 | A | 1/1999 | Thompson et al. | |
| 5,899,906 | A | 5/1999 | Schenk | |
| 5,899,909 | A | 5/1999 | Claren et al. | |
| 5,899,999 | A | 5/1999 | De Bonet | |
| 5,934,283 | A | 8/1999 | Willem et al. | |
| 5,935,122 | A | 8/1999 | Fourkas et al. | |
| 5,945,122 | A | 8/1999 | Abra et al. | |
| 5,954,057 | A | 9/1999 | Li | |
| 5,997,554 | A | 12/1999 | Thompson | |
| 6,010,447 | A | 1/2000 | Kardjian | |
| 6,030,393 | A | 2/2000 | Corlew | |
| 6,039,686 | A | 3/2000 | Kovac | |
| 6,042,534 | A | 3/2000 | Gellman et al. | |
| 6,050,937 | A | 4/2000 | Benderev | |
| 6,053,935 | A | 4/2000 | Brenneman et al. | |
| 6,096,041 | A | 8/2000 | Gellman et al. | |
| 6,099,547 | A | 8/2000 | Gellman et al. | |
| 6,110,101 | A | 8/2000 | Tihon et al. | |
| 6,117,067 | A | 9/2000 | Gil-Vernet | |
| 6,200,330 | B1 | 3/2001 | Benderev et al. | |
| 6,221,005 | B1 | 4/2001 | Bruckner et al. | |
| 6,221,084 | B1 | 4/2001 | Fleenor | |
| 6,264,676 | B1 | 7/2001 | Gellman et al. | |
| 6,273,852 | B1 | 8/2001 | Lehe et al. | |
| 6,306,079 | B1 | 10/2001 | Trabucco | |
| 6,334,446 | B1 | 1/2002 | Beyar | |
| 6,382,214 | B1 | 5/2002 | Raz et al. | |
| 6,406,423 | B1 | 6/2002 | Scetbon | |
| 6,423,072 | B1 | 7/2002 | Zappala | |
| 6,423,080 | B1 | 7/2002 | Gellman et al. | |
| 6,475,139 | B1 | 11/2002 | Miller | |
| 6,478,727 | B2 | 11/2002 | Scetbon | |
| 6,491,703 | B1 * | 12/2002 | Ulmsten | 606/144 |
| 6,494,887 | B1 | 12/2002 | Kaladelfos | |
| 6,530,943 | B1 | 3/2003 | Hoepffner et al. | |
| 6,582,443 | B2 | 6/2003 | Cabak et al. | |
| 6,596,001 | B2 | 7/2003 | Stormby et al. | |
| 6,596,002 | B2 | 7/2003 | Therin et al. | |
| 6,599,235 | B2 | 7/2003 | Kovac | |
| 6,605,097 | B1 * | 8/2003 | Lehe et al. | 606/148 |
| 6,612,977 | B2 | 9/2003 | Staskin et al. | |
| 6,638,209 | B2 | 10/2003 | Landgrebe | |
| 6,638,210 | B2 | 10/2003 | Berger | |
| 6,638,211 | B2 | 10/2003 | Suslian et al. | |
| 6,641,525 | B2 | 11/2003 | Rocheleau et al. | |
| 6,648,921 | B2 | 11/2003 | Anderson et al. | |
| 6,652,450 | B2 | 11/2003 | Neisz et al. | |
| 6,685,629 | B2 | 2/2004 | Therin | |
| 6,691,711 | B2 | 2/2004 | Raz et al. | |
| 6,730,110 | B1 | 5/2004 | Harari et al. | |
| 6,755,781 | B2 | 6/2004 | Gellman | |
| 6,802,807 | B2 | 10/2004 | Anderson et al. | |
| 6,830,052 | B2 | 12/2004 | Carter et al. | |
| 6,932,759 | B2 | 8/2005 | Kammerer et al. | |
| 7,070,556 | B2 * | 7/2006 | Anderson et al. | 600/29 |
| 7,387,634 | B2 | 6/2008 | Benderev | |
| 7,524,281 | B2 | 4/2009 | Chu et al. | |
| 8,449,573 | B2 | 5/2013 | Chu | |
| 2001/0018549 | A1 | 8/2001 | Scetbon | |
| 2001/0049467 | A1 | 12/2001 | Lehe et al. | |
| 2002/0028980 | A1 | 3/2002 | Thierfelder et al. | |
| 2002/0058959 | A1 | 5/2002 | Gellman | |
| 2002/0072694 | A1 | 6/2002 | Snitkin et al. | |
| 2002/0077526 | A1 | 6/2002 | Kammerer et al. | |
| 2002/0091373 | A1 | 7/2002 | Berger | |
| 2002/0116025 | A1 | 8/2002 | Haab | |
| 2002/0120277 | A1 * | 8/2002 | Hauschild et al. | 606/108 |
| 2002/0128670 | A1 | 9/2002 | Ulmsten et al. | |
| 2002/0138025 | A1 | 9/2002 | Gellman et al. | |
| 2002/0147382 | A1 | 10/2002 | Neisz et al. | |
| 2002/0151910 | A1 | 10/2002 | Gellman et al. | |
| 2002/0161382 | A1 | 10/2002 | Neisz et al. | |
| 2002/0188169 | A1 | 12/2002 | Kammerer et al. | |
| 2002/0188301 | A1 | 12/2002 | Dallara et al. | |
| 2003/0004395 | A1 | 1/2003 | Therin | |
| 2003/0004580 | A1 | 1/2003 | Sump et al. | |
| 2003/0009181 | A1 | 1/2003 | Gellman et al. | |
| 2003/0010929 | A1 | 1/2003 | Priewe et al. | |
| 2003/0023135 | A1 | 1/2003 | Ulmsten et al. | |
| 2003/0023138 | A1 | 1/2003 | Luscombe | |
| 2003/0028075 | A1 | 2/2003 | Ulmsten et al. | |
| 2003/0050530 | A1 | 3/2003 | Neisz et al. | |
| 2003/0100954 | A1 | 5/2003 | Schuldt-Hempe et al. | |
| 2003/0130670 | A1 | 7/2003 | Anderson et al. | |
| 2003/0149440 | A1 | 8/2003 | Kammerer et al. | |
| 2003/0171644 | A1 | 9/2003 | Anderson et al. | |
| 2003/0176762 | A1 | 9/2003 | Kammerer | |
| 2003/0195386 | A1 | 10/2003 | Thierfelder et al. | |

(56) References Cited

U.S. PATENT DOCUMENTS

| | | |
|---|---|---|
| 2003/0220538 A1 | 11/2003 | Jacquetin |
| 2004/0039453 A1 | 2/2004 | Anderson et al. |
| 2005/0228406 A1* | 10/2005 | Bose .................. 606/144 |
| 2006/0089525 A1* | 4/2006 | Mamo et al. .............. 600/37 |
| 2006/0173491 A1* | 8/2006 | Meade et al. ............ 606/222 |
| 2006/0217589 A1 | 9/2006 | Wan et al. |
| 2006/0229596 A1* | 10/2006 | Weiser et al. ............ 606/37 |
| 2008/0103527 A1 | 5/2008 | Martin et al. |
| 2010/0268255 A1 | 10/2010 | Ostrovsky et al. |
| 2010/0324357 A1 | 12/2010 | Chu |
| 2011/0106108 A1 | 5/2011 | Ostrovsky et al. |

FOREIGN PATENT DOCUMENTS

| | | |
|---|---|---|
| DE | 4334419 A1 | 4/1995 |
| DE | 10103179 A1 | 7/2001 |
| EP | 0598976 A2 | 6/1994 |
| EP | 0599772 A1 | 6/1994 |
| EP | 0688056 A1 | 12/1995 |
| EP | 0774240 A1 | 5/1997 |
| EP | 0941712 A1 | 9/1999 |
| EP | 1025811 A2 | 8/2000 |
| RU | 1225547 A | 4/1986 |
| RU | 1443873 A1 | 12/1988 |
| SE | 503271 C2 | 4/1996 |
| WO | 90/03766 A1 | 4/1990 |
| WO | 96/06567 A1 | 3/1996 |
| WO | 96/06597 A1 | 3/1996 |
| WO | 97/13465 A1 | 4/1997 |
| WO | 98/31301 A1 | 7/1998 |
| WO | 98/34545 A1 | 8/1998 |
| WO | 00/74594 A1 | 12/2000 |
| WO | 01/06951 A1 | 2/2001 |
| WO | 02/26108 A2 | 4/2002 |
| WO | 02/28312 A1 | 4/2002 |
| WO | 02/38079 A2 | 5/2002 |
| WO | 2004/012626 A1 | 2/2004 |
| WO | 2005/122954 A1 | 12/2005 |
| WO | 2006/108145 A1 | 10/2006 |
| WO | 2008/087635 A2 | 7/2008 |
| WO | 2010/065274 A1 | 6/2010 |

OTHER PUBLICATIONS

Non Final Office Action Response for U.S. Appl. No. 12/549,704, filed on Dec. 23, 2011, 27 pages.

Non Final Office Action Response for U.S. Appl. No. 12/549,704, filed on Oct. 25, 2012, 8 pages.

Notice of Allowance for U.S. Appl. No. 12/549,704, mailed on Feb. 1, 2013, 10 pages.

* cited by examiner

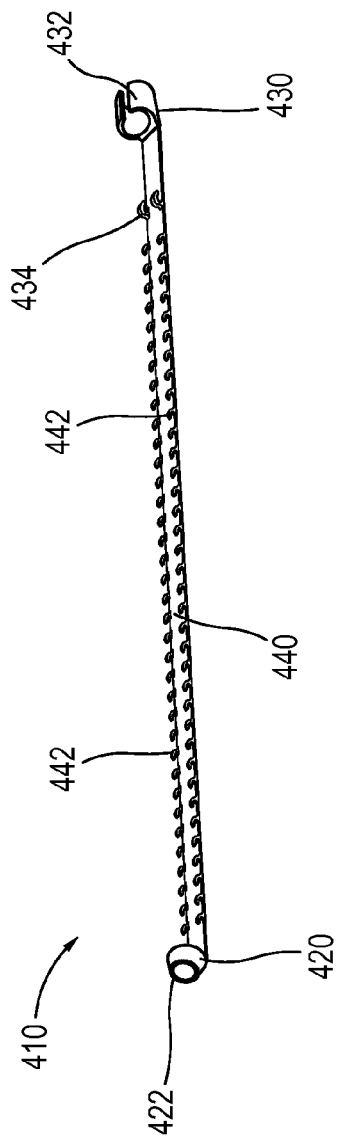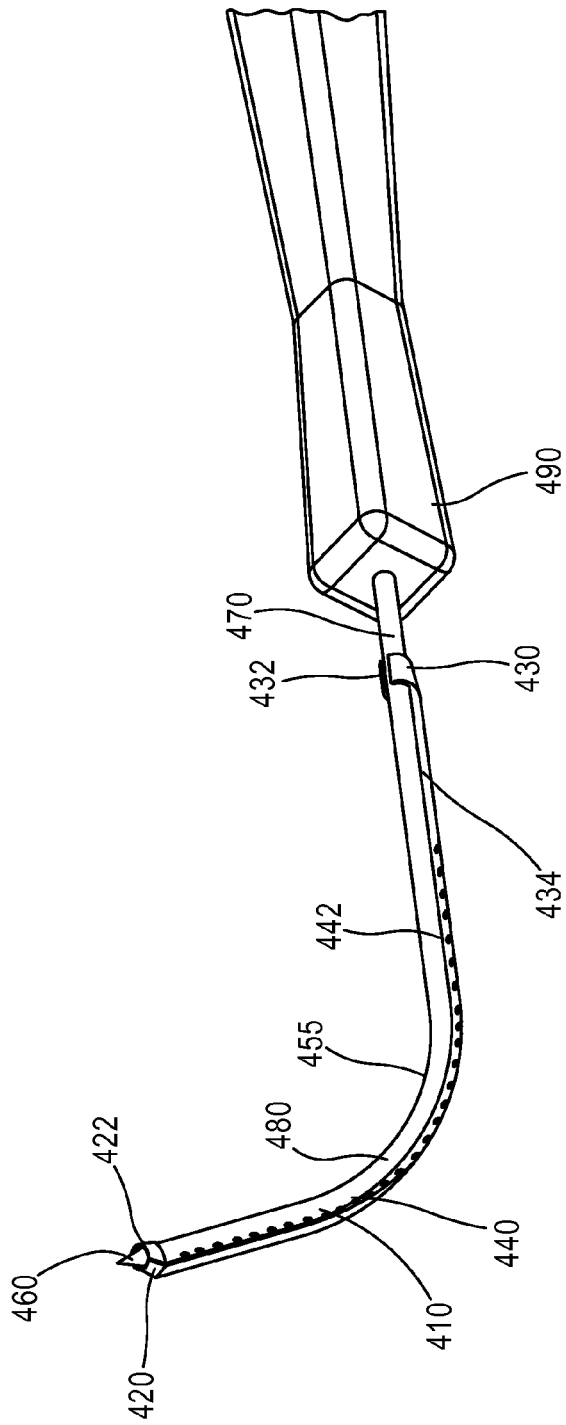

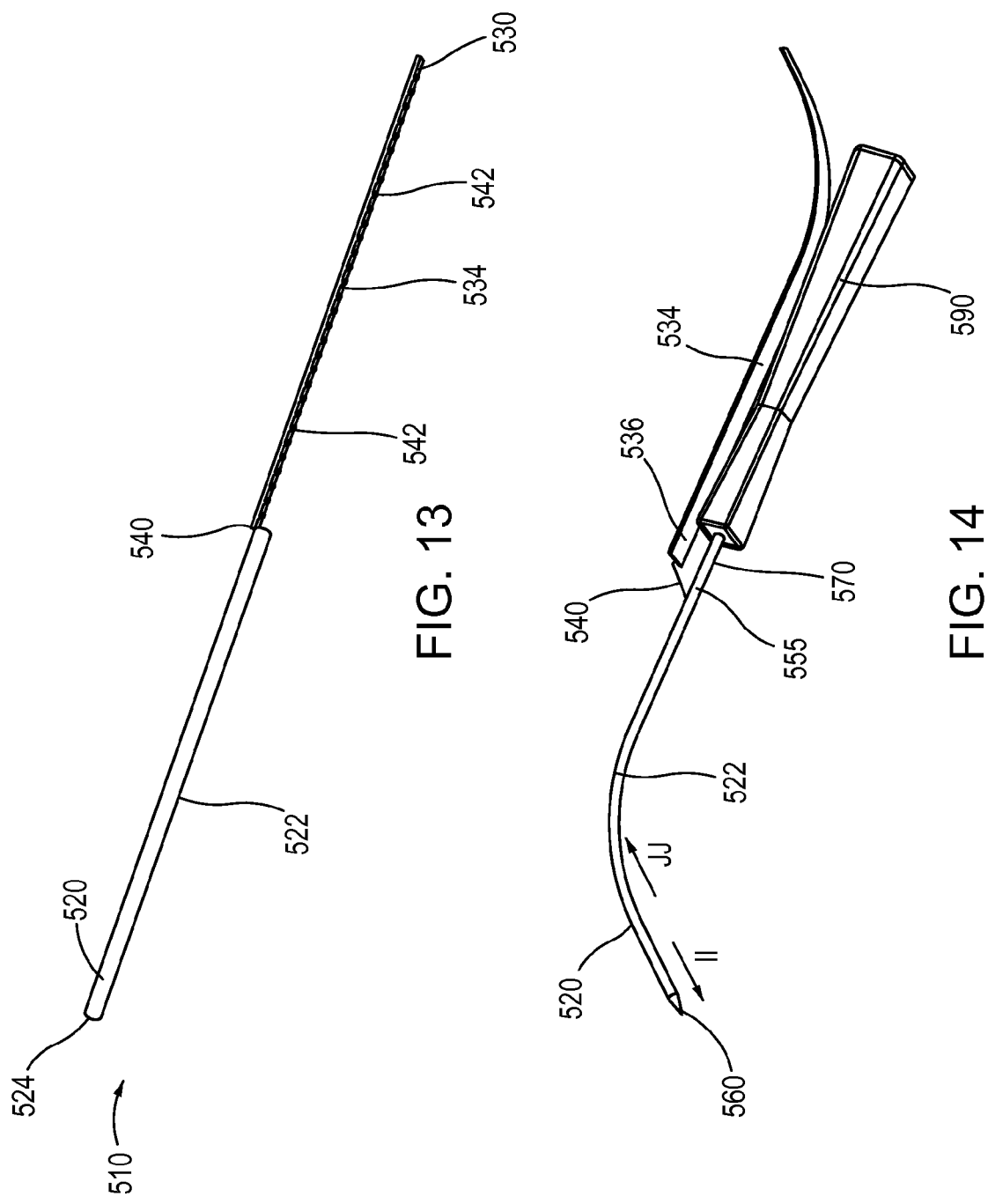

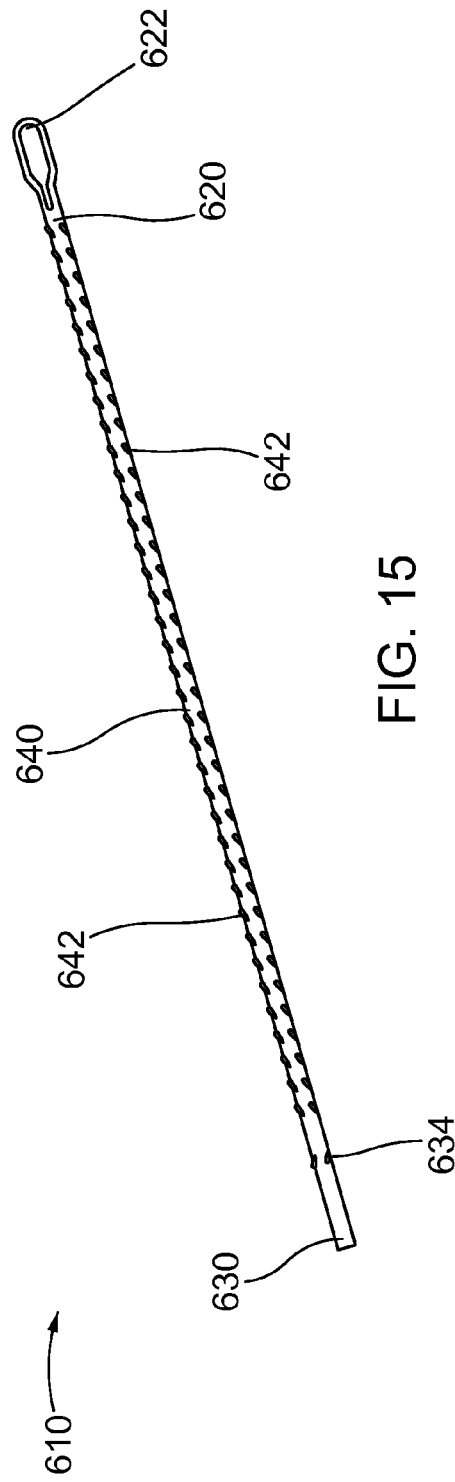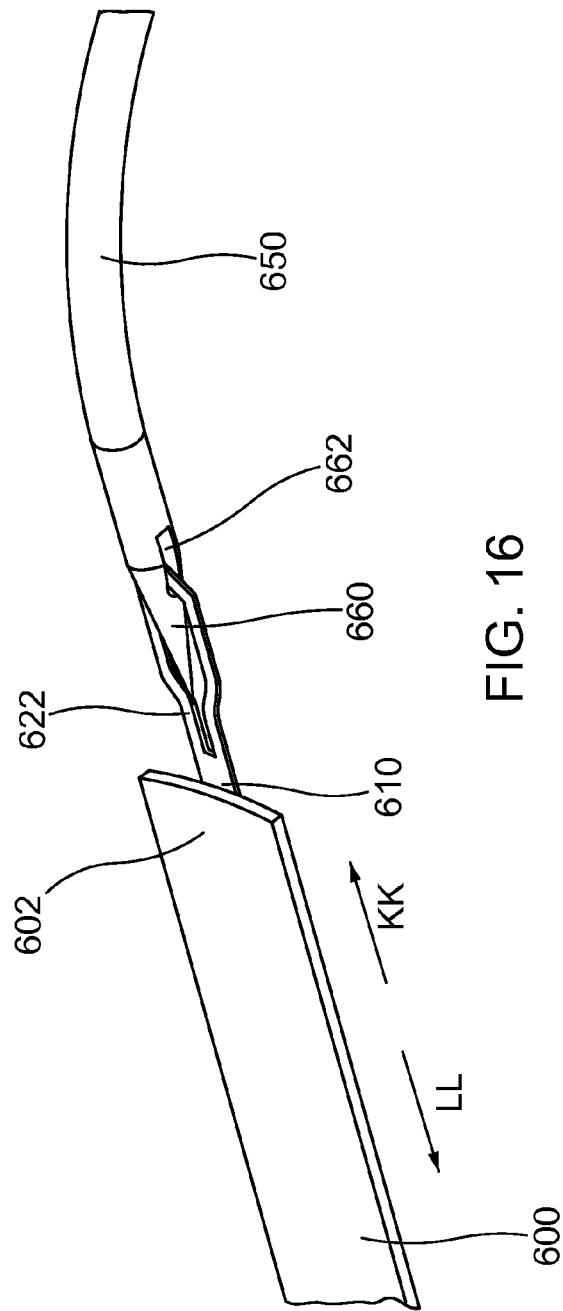

US 9,301,750 B2

DEVICE AND METHOD FOR DELIVERY OF MESH-BASED DEVICES

RELATED APPLICATION

This application claims priority to and the benefit of U.S. Provisional Patent Application Ser. No. 61/257,616, filed on Nov. 3, 2009, entitled, "Device and Method for Delivery of Mesh-Based Devices," which is incorporated herein by reference in its entirety.

BACKGROUND

The disclosed embodiments relate generally to medical devices and more particularly to an insertion device for delivery of a mesh implant into a body of a patient.

The disclosed embodiments have application to a wide variety of surgical procedures. For example, one such procedure is directed to urinary incontinence and includes fixing an implant to tissue within a body of a patient to provide support for the urethra. Another such procedure includes fixing an implant to bodily tissue of a patient to support a bladder of the patient.

In some procedures, it is necessary for a practitioner, such as a physician, to insert a mesh implant into bodily tissue of the patient at a location not easily visible to the practitioner. In such procedures, known insertion devices can be used to position a mesh implant at a first location within bodily tissue and to fix the mesh implant to the tissue. However, when the mesh implant is uncoupled from the insertion device and the insertion device removed from the tissue of the patient, the mesh implant can be inadvertently moved from its intended position. In such instances, misplacement of the mesh implant can occur. If misplacement of the mesh implant occurs, the practitioner can remove or pull out the misplaced mesh implant and attempt to replace the implant within the tissue of the patient. This can cause severe and/or unnecessary trauma to the patient. Further, during insertion, the mesh implant can be stretched causing the implant to be misplaced.

Thus, a need exists for an insertion device that permits the mesh implant to remain at an intended location within bodily tissue once the mesh implant has been inserted into the tissue and during removal from of the insertion device. A need also exists for an insertion device having a configuration that facilitates deployment of the mesh implant from the insertion device. A need also exists for an insertion device that reduces the amount an implant is stretched when inserted into a tissue of a patient.

SUMMARY

In some embodiments, a stylet includes a proximal end portion, a distal end portion, and a medial portion between the proximal end portion and the distal end portion. The distal end portion of the stylet is configured to be releasably coupled to a first portion of an implant. The medial portion of the stylet has at least one retention member configured to be releasably coupled to a second portion of the implant.

BRIEF DESCRIPTION OF THE DRAWINGS

FIG. 10 is a perspective view of an elongate member having a plurality of retention members, according to another embodiment.

FIG. 11 is a perspective view of the elongate member of FIG. 10 coupled to an insertion device.

FIG. 13 is a perspective view of an elongate member including a first portion having a plurality of retention members and a second portion having a dilator, according to another embodiment.

FIG. 14 is a perspective view of the elongate member of FIG. 13 coupled to an insertion device.

FIG. 15 is a perspective view an elongate member having a plurality of retention members, according to another embodiment.

FIG. 16 is a perspective view of an implant coupled to an insertion device, according to another embodiment.

DETAILED DESCRIPTION

Figure 1:
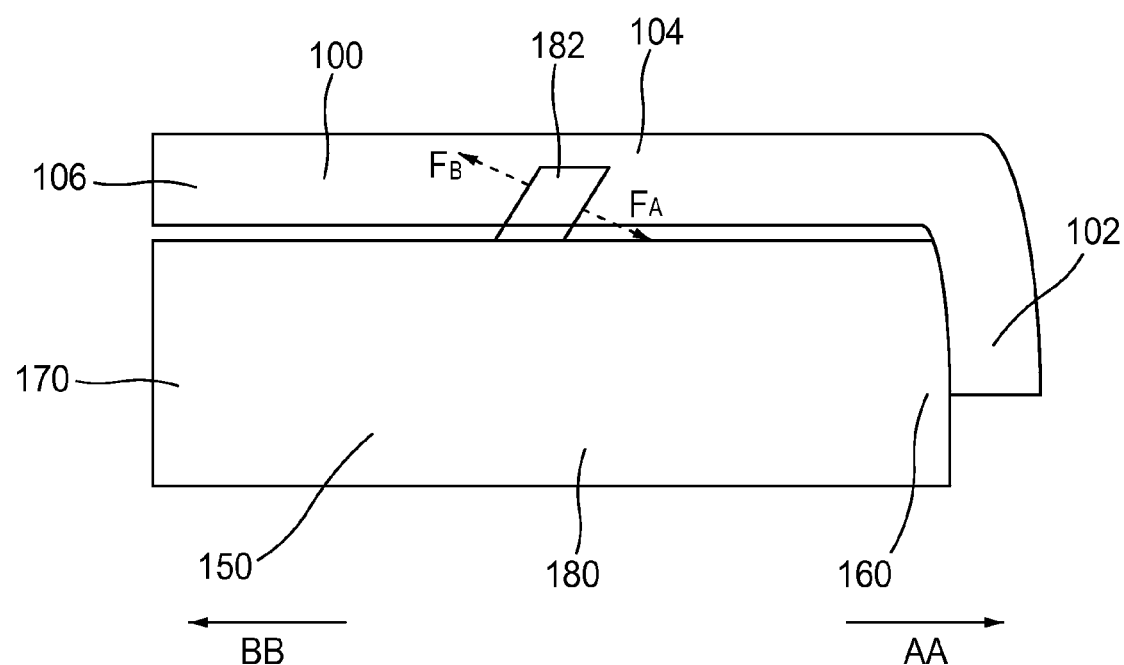
FIG. 1 is a schematic illustration of an implant coupled to an insertion device, according to an embodiment.
Figure 2:
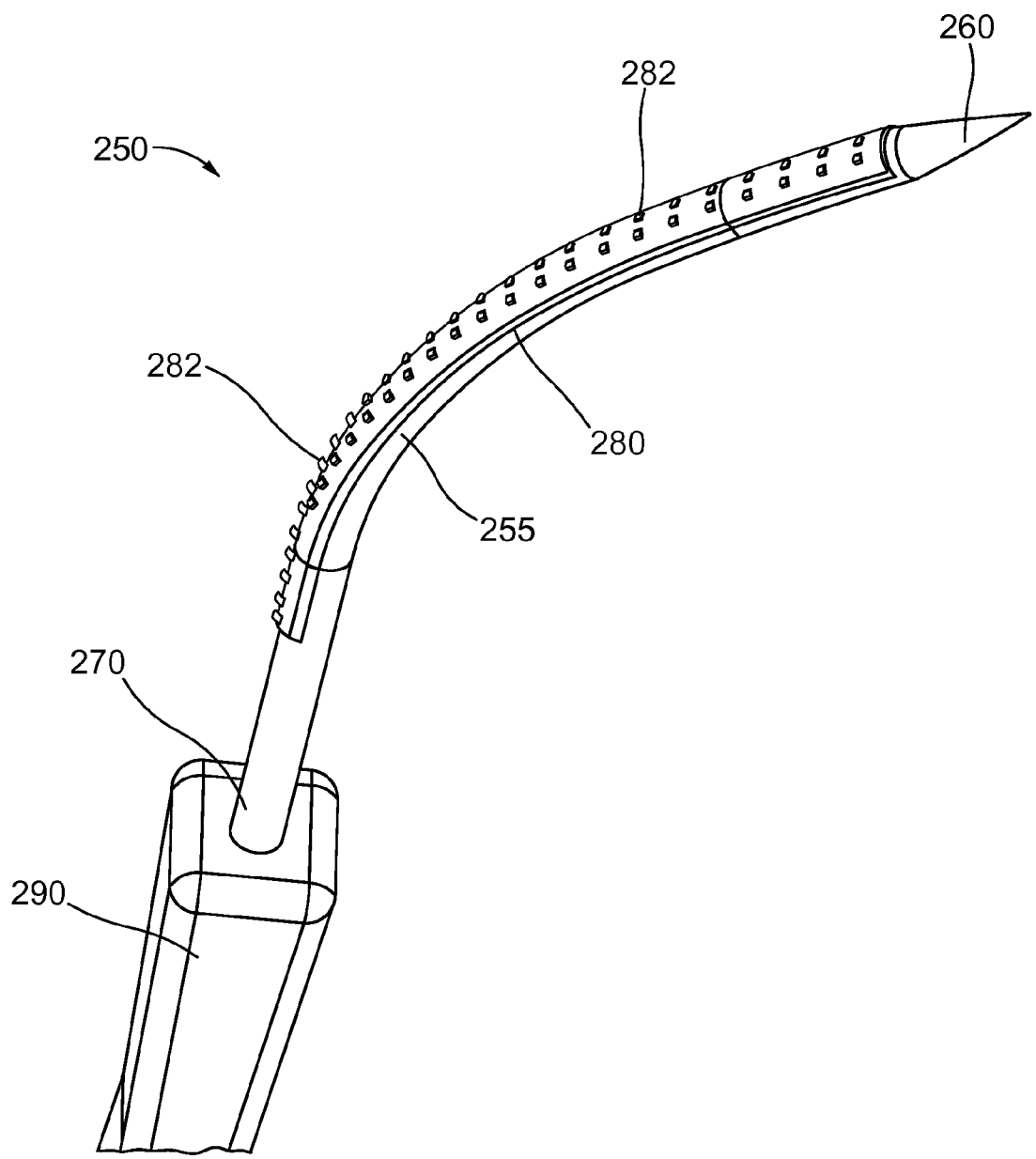
FIG. 2 is a perspective view of an insertion device, according to another embodiment.

In some embodiments, an insertion device includes a stylet and a handle portion. The stylet includes a proximal end portion, a distal end portion, and a medial portion between the proximal end portion and the distal end portion. The distal end portion of the stylet is configured to be releasably coupled to a first portion of an implant. The medial portion of the stylet has at least one retention member configured to be releasably coupled to a second portion of the implant.

In some embodiments, an insertion device includes an elongate member having a retention member and at least one coupling mechanism. The at least one coupling mechanism is configured to releasably couple the elongate member to a stylet used to insert an implant into a tissue of a patient. The retention member is configured to releasably couple at least a portion of the implant to at least a portion of the elongate member.

In some embodiments, a medical device includes a stylet, an elongate member, and an implant. The elongate member has a distal end portion, a proximal end portion and a medial portion. The medial portion of the elongate member has a retention member. The elongate member is configured to be coupled to the stylet. The implant has a distal end portion, a proximal end portion and a medial portion. The distal end portion of the implant is configured to be coupled to the distal end portion of the elongate member. The medial portion of the implant is configured to be releasably coupled to the elongate member via the retention member.

In some embodiments, a method of inserting an implant includes coupling a distal end portion of an elongate member to a distal end portion of a stylet. The distal end portion of the implant is coupled to the distal end portion of the elongate member. A medial portion of the implant is releasably coupled to a medial portion of the elongate member. The method further includes inserting the distal end portion of the stylet into a tissue of a patient by moving the stylet with respect to the tissue in a first direction, uncoupling the distal end portion of the elongate member from the distal end portion of the stylet, removing the distal end portion of the stylet from the tissue of the patient, uncoupling the distal end portion of the implant from the distal end portion of the elongate member, and moving the elongate member with respect to the tissue in a second direction, different from the first direction, such that the medial portion of the implant is uncoupled from the medial portion of the elongate member.

An implant according to an embodiment of the invention can include one or more tanged portions and/or one or more detanged portions. The terms "tanged" or "tangs" as used herein mean roughened or jagged edges or areas, such as can result from cutting a woven or knit mesh material. The tanged portion can be used, for example, to anchor or secure the implant to tissue.

As used herein, the terms proximal portion or proximal end refer to the portion or end, respectively, of a device that is closest to a medical practitioner (e.g., a physician) when performing a medical procedure, and the terms distal portion or distal end refer to the portion or end, respectively, of the device that is furthest from the physician during a medical procedure. For example, the end of a medical device first inserted inside the patient's body would be the distal end of the medical device, while the end of the medical device handled by the medical practitioner would be the proximal end of the medical device.

FIG. 1 is a schematic illustration of an implant 100 coupled to an insertion device 150, according to an embodiment. The implant 100 includes a first end portion 102, a second end portion 106, and a medial portion 104. In some embodiments, the first end portion 102 of the implant 100 is coupled to a distal end portion 160 of the insertion device 150. In some embodiments, the medial portion 104 of the implant 100 is coupled to a medial portion 180 of the insertion device 150, as further described herein.

The implant 100 can be configured to be placed within a body of a patient and can be configured to support a portion of the body. For example, the implant 100 can be similar to the implants or grafts disclosed in U.S. Patent Application No. 61/017,257 to Chu et al., entitled "Apparatus and Method for Uterine Preservation," filed on Dec. 28, 2007, the disclosure of which is hereby incorporated by reference in its entirety. The implant 100 can be a variety of different shapes, sizes and configurations depending on the intended use for the particular implant. In some embodiments, the implant 100 can be substantially rectangular, square, oval, or elliptical. The implant 100 can be shaped and sized to support a bladder and/or a bladder neck (e.g., to treat a cystocele), a uterus (e.g., to treat a hysterocele) and/or a rectum (e.g. to treat a rectocele). In some embodiments, for example, the implant 100 is a filament, a tape, a sling, and/or a strap. In some embodiments, the implant is a mesh strap having a length less than 10 inches. In other embodiments, the implant has a length greater than 10 inches.

The implant 100 can be formed with a mesh material to allow tissue in-growth to the implant 100 after implantation. For example, some or all of the implant 100 can be formed with a mesh material as described in U.S. Patent Pub. 2005/0038452 to Chu, entitled "Medical Slings," filed on Aug. 14, 2003, the disclosure of which is hereby incorporated by reference in its entirety. In some embodiments, some or all of the implant 100 can be formed with the Advantage® Mesh or the Polyform™ Synthetic Mesh material each provided by Boston Scientific Corporation.

In some embodiments the implant 100 includes one or more tanged portions (as described above). The tangs allow the implant 100 to be anchored within pelvic tissue without the use of additional anchoring mechanisms or sutures. In some embodiments, for example, the implant 100 includes a tanged portion to engage and help secure the implant 100 to pelvic tissue. Pelvic tissue can include, for example, ligaments (such as a sacrospinous ligament), muscle (such as an obturator internus muscle or an obturator externus muscle), fascia, or any other structure or tissue within a pelvic region of a patient. In some embodiments, an implant 100 includes tangs on an edge along an entire length of the implant 100. In other embodiments, the implant includes tangs covering substantially all of an exterior surface of the implant.

In some embodiments, the implant 100 includes an anchor on the first end portion 102 and/or the second end portion 106. The anchors can be similar to the mesh carriers shown and described in U.S. Patent Application No. 61/193,542 to Chu, entitled "Insertion Device and Method for Delivery of a Mesh Carrier," filed on Dec. 5, 2008, the disclosure of which is hereby incorporated by reference in its entirety. In such embodiments, the anchor is configured to be inserted into a tissue of a patient to retain the implant 100 within the body of the patient when the implant 100 supports a portion of the body of the patient. Additionally, the anchor can be used to couple the first end portion 102 of the implant 100 to the distal end portion 160 of the insertion device 150.

In some embodiments, the insertion device 150 can place the anchor and/or the end portions 102, 106 of the implant 100 into the obturator externus muscle for incontinence treatment. Specifically, in some embodiments, an anchor coupled to the first end portion 102 of the implant 100 and/or the first end portion 102 of the implant 100 and an anchor coupled to the second end portion 106 of the implant 100 and/or the second end portion 106 of the implant 100 are placed in opposing obturator externus muscles of a patient and the filament is extended between the end portions 102, 106 of the implant 100 to form a sling to provide support to the urethra or bladder neck of the patient.

The insertion device has a proximal end portion 170, a distal end portion 160, and a medial portion 180 between the proximal end portion 170 and the distal end portion 160. In some embodiments, the distal end portion 160 has a tapered portion configured to penetrate a tissue of a patient. In such embodiments, for example, the tapered portion can have a sharp tip such that tissue is penetrated and/or dilated when the distal end portion 160 is inserted into a tissue of a patient.

In some embodiments, the distal end portion 160 includes a coupling mechanism (not shown in FIG. 1) configured to releasably couple the first end portion 102 of the implant 100 to the distal end portion 160 of the insertion device 150. In such embodiments, the coupling mechanism can include anything suitable to releasably couple the first end portion 102 of the implant 100 to the distal end portion 160 of the insertion device 150. In some embodiments, for example, the coupling mechanism is a snap-fit connector, a protrusion that fits into a lumen defined by the first end portion 102 of the implant 100, hooks, an adhesive, a staple, and/or the like.

In some embodiments, the first end portion 102 of the implant 100 is uncoupled from the distal end portion 160 of the insertion device 150 by sliding an outer member (not shown in FIG. 1) of the insertion device 150 with respect to the distal end portion 160 of the insertion device 150 in the direction shown by the arrow AA in FIG. 1. The outer member can contact and apply a force to the first end portion 102 of the implant 100 that causes the first end portion 102 of the implant 100 to uncouple from the distal end portion 160 of the insertion device 150. In such embodiments, the outer member of the insertion device 150 can be similar to the elongate members of the insertion devices shown and described in U.S. Provisional Patent Application No. 61/120,105, to Chu, filed Dec. 5, 2008 and entitled "Insertion Device and Method for Delivery of a Mesh Carrier," the disclosure of which is hereby incorporated by reference in its entirety.

In other embodiments, the medical practitioner can unsnap the first end portion of the implant from the insertion device, remove the first end portion of the implant from the implant, cut the first end portion of the implant, and/or use any method suitable to uncouple the first end portion of the implant from the insertion device. In such embodiments, the distal end portion of the insertion device can be passed entirely through a tissue such that the medical practitioner has access to the distal end portion of the insertion device and the first end portion of the implant when the medial portion of the insertion device and the medial portion of the implant are disposed within the tissue. In some embodiments, for example, the distal end portion of the insertion device is passed through the tissue and outside a body of the patient. In other embodiments, the distal end portion of the implant is passed through the tissue to an area within the body of the patient that the medical practitioner can access. In other embodiments, the first end portion of the implant is uncoupled from the distal end portion of the insertion device when the medical practitioner moves the insertion device in the direction shown by the arrow BB in FIG. 1.

The medial portion 180 of the insertion device 150 includes a retention member 182. The retention member 182 is configured to releasably couple the medial portion 104 of the implant 100 to the medial portion 180 of the insertion device 150. In some embodiments, the retention member 182 is a hook. In such embodiments, the hook is configured to be inserted into an aperture defined by the implant 100. In some embodiments, the aperture defined by the implant 100 can be defined by the weave or knit structure of the implant 100.

In some embodiments, a width of the implant 100 is greater than a width of the insertion device 150. The implant 100 contacts surrounding tissue when the insertion device 150 is removed from the tissue of the patient. The friction between the implant 100 and the surrounding tissue helps retain the position of the implant 100 as the insertion device 150 is removed from the tissue.

In some embodiments, the implant 100 is configured to remain coupled to the insertion device 150 when the insertion device 150 is moved within a tissue in a first direction (shown by AA in FIG. 1) but uncouple from the insertion device 150 when the insertion device is moved through a tissue in a second direction (shown by BB in FIG. 1). In such embodiments, the retention member 182 can be disposed at an angle to the insertion device 180 such that the retention member applies a force $F_A$ on the implant 100 when the insertion device 150 is moved in the first direction AA. The force $F_A$ is configured to keep the implant coupled to the insertion device 150 and move the implant 100 in the first direction AA when the insertion device 150 is moved in the first direction AA.

When the insertion device 150 is moved in the second direction BB, the insertion device 150 applies a force $F_B$ to the implant 100. The force $F_B$ causes the implant 100 to uncouple from the insertion device 150 when the insertion device 150 is moved in the second direction BB. In some embodiments, the retention member is a hook that defines an opening facing the distal end portion 160 of the insertion device 150 but not the proximal end portion 170 of the insertion device such that the hook retains the medial portion 104 of the implant 100 when the insertion device 150 is moved in the first direction but releases the medial portion 104 of the implant 100 through the opening when moving in the second direction (see e.g., FIG. 7).

In some embodiments, the retention member 182 has a height that is less than a height of the implant 100. For example, the retention member 182 has a height that is less than the height of individual strands of a mesh implant 100. In such embodiments, the retention member 182 contacts a portion of the individual strand when moved in the direction shown by the arrow AA in FIG. 1. In other embodiments, for example, a hook can be positioned through an aperture defined by a mesh implant and over a strand of the mesh. The height of the hook is larger than the height of the individual strand, but not larger than the height of the implant as a whole. For example, if the implant is constructed of woven mesh, a height of an individual strand is less than the height of the hook, but the height of a knot of the mesh is greater than the height of the hook. In such embodiments, because the height of the hook is less than a height of the implant (e.g., the knot of the mesh), the hook minimally contacts the surrounding tissue as the insertion device and the implant are inserted into a tissue of a patient.

In some embodiments, the proximal end portion 170 of the insertion device 150 includes a handle. A medical practitioner can use the handle to control and/or guide the insertion device 150 when inserting the insertion device 150 into a body of a patient.

In use, the first end portion 102 of the implant 100 is coupled to the distal end portion 160 of the insertion device 150 and the medial portion 104 of the implant 100 is coupled to the medial portion 180 of the insertion device 150, as described above. The implant 100 and the insertion device 150 can then be inserted into a tissue of a patient.

The implant 100 and the insertion device 150 are inserted into the tissue of the patient in the direction shown by the arrow AA in FIG. 1. In embodiments where the insertion device 150 includes a tapered portion, the tapered portion penetrates and dilates the tissue as the insertion device 150 and the implant 100 are inserted. The coupling mechanism of the distal end portion 160 of the insertion device 150 and the retention member 182 of the medial portion 180 of the insertion device 150 keep the implant 100 coupled to the insertion device 150 as the insertion device 150 and the implant 100 are moved in the direction shown by the arrow AA in FIG. 1.

Once the implant 100 is positioned at a desired location within the tissue, the first end portion 102 of the implant 100 is uncoupled from the distal end portion 160 of the insertion device 150. Depending on the type of coupling mechanism used, this can be done by any suitable method, as described above.

The insertion device 150 can then be moved through the tissue in the direction shown by the arrow BB in FIG. 1. Moving the insertion device in the direction shown by the arrow BB uncouples the medial portion 104 of the implant 100 from the medial portion 180 of the insertion device 150, as described above. In some embodiments, the retention member 182 applies a force $F_B$ on the implant 100 that uncouples the implant 100 from the insertion device 150.

The implant 100 engages the surrounding tissue and remains within the tissue as the insertion device 150 is removed from the tissue. In some embodiments, tanged portions of the implant 100 are used to engage the tissue. In other embodiments, an anchor secures the implant in the tissue as the insertion device is removed from the tissue.

Once the first end portion 102 of the implant 100 is disposed within the tissue of the patient, the second end portion 106 of the implant can be similarly placed within the tissue of the patient such that the medial portion 104 of the implant can support a portion of the body of the patient.

FIGS. 2-5B show an insertion device 250 and an implant 200, according to another embodiment. The implant 200 includes a first end portion 202, a second end portion 206 and a medial portion 204. In some embodiments, the first end portion 202 and the second end portion 206 can include coupling portions configured to couple the implant 200 to a stylet 255, as further described in detail herein. In such embodiments, the coupling portions define lumens configured to receive a portion of the stylet 255. In other embodiments, the coupling portions define lumens configured to receive a hook coupled to the stylet and/or the like. In still other embodiments, the coupling portions can be a portion of a snap connector and/or the like. The implant 200 is similar to the implant 100. In some embodiments, for example, the implant 200 is constructed of a knitted or woven mesh.

The insertion device 250 includes a handle 290 and a stylet 255. The handle 290 can be any suitable handle that allows a medical practitioner to control and/or guide the stylet 255 when inserting the stylet 255 into a body of a patient. The handle 270 is coupled to a proximal end portion 270 of the stylet 255.

The stylet 255 includes a distal end portion 260, a proximal end portion 270 and a medial portion 280 between the distal end portion 260 and the proximal end portion 270. In the illustrated embodiment, the stylet 255 is curved. This allows a medical practitioner to insert an implant 200 (see FIG. 4) into difficult to reach tissues. For example, the curved stylet 255 allows a medical practitioner to maneuver around a portion of a body of a patient and insert the implant 200 into tissue obstructed by the portion of the body. In other embodiments, the stylet is straight.

Figure 5A:
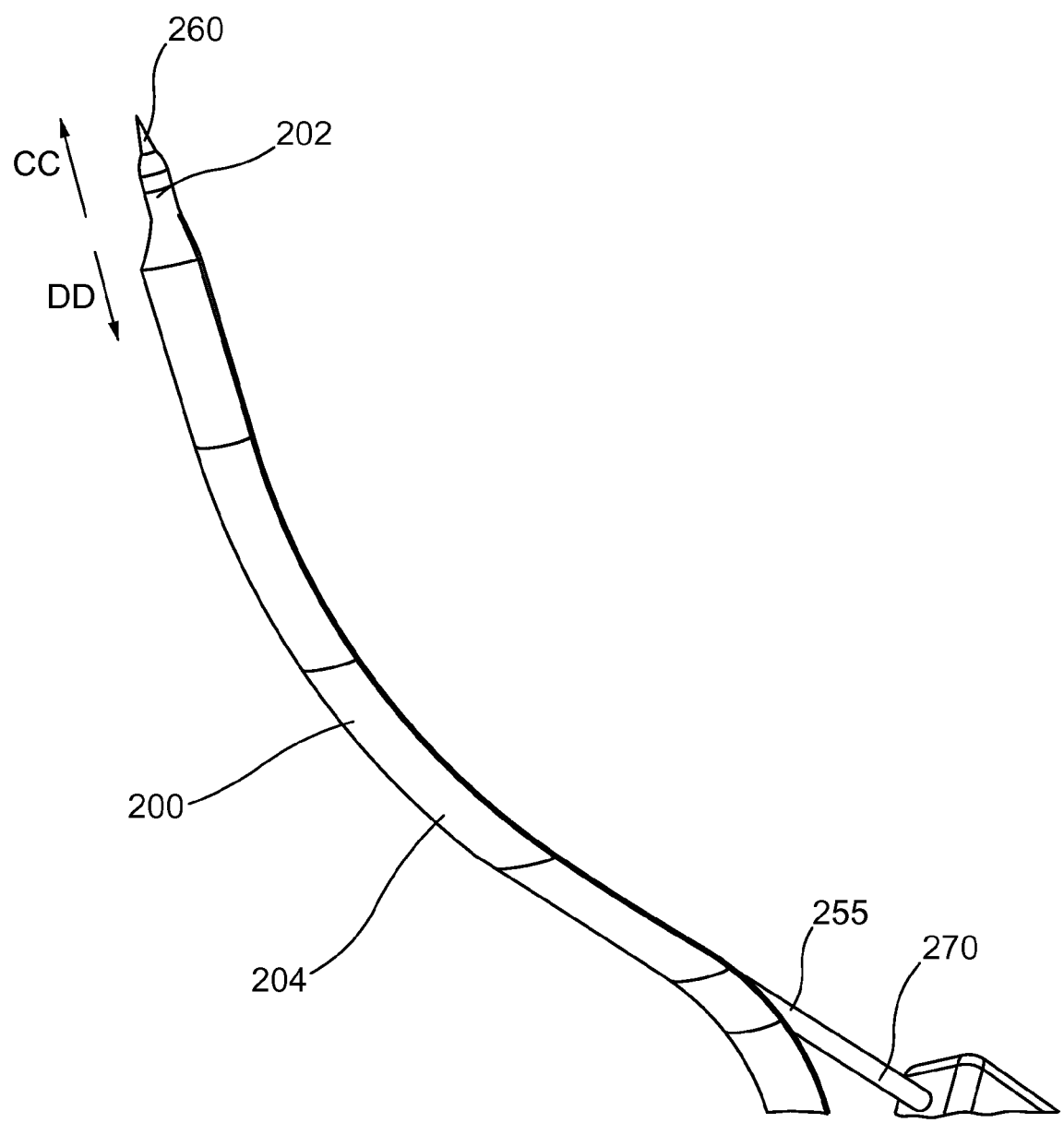
FIG. 5A is a perspective view of the implant of FIG. 4 coupled to an insertion device.

The distal end portion 260 of the stylet 255 is configured to be coupled to the first end portion 202 of an implant 200 (see FIG. 5A). As described above, and as shown in FIG. 5A, in some embodiments, the first end portion 202 of the implant 200 defines a lumen configured to receive the distal end portion 260 of the stylet 255. In some embodiments, the distal end portion 260 of the stylet 255 can be wrapped to define the lumen. The distal end portion 260 of the stylet 255 is tapered such that the distal end portion 260 is configured to pierce and/or dilate a tissue as the stylet 255 is inserted into the tissue. A portion of the distal end portion 260 of the stylet 255 with the largest cross-section (e.g., diameter), has a cross-section larger than the lumen defined by the first end portion 202 of the implant 200. Accordingly, the first end portion 202 of the implant 200 remains coupled to the stylet 255 when the stylet 255 is moved in a direction shown by the arrow CC in FIGS. 3 and 5A, but uncouples from the stylet 255 when the stylet 255 is moved in a direction shown by the arrow DD in FIGS. 3 and 5A. In other embodiments, the first end portion of the implant is coupled to the distal end portion of the stylet by other means. In some embodiments, for example, a snap connector, a hook, an adhesive, a staple and/or the like is used to couple the first end portion of the implant to the distal end portion of the stylet.

The medial portion 280 of the stylet 255 includes multiple retention members 282. The retention members 282 are configured to be disposed within apertures defined by a medial portion 204 of the implant 200. The retention members 282 are angled toward the distal end portion 260 of the stylet 255 such that a free end of each retention member 282 is closer to the distal end portion 260 of the stylet 255 than an end of each retention member 282 coupled to the stylet 255. This allows the retention members 282 to retain the medial portion 204 of the implant 200 when the stylet 255 is moved substantially in a direction shown by the arrow CC in FIGS. 3 and 5A. Specifically, when the stylet 255 is moved substantially in the direction shown by the arrow CC in FIGS. 3 and 5A, the retention members 282 exert a force on the medial portion 204 of the implant 200 that causes the medial portion 204 of the implant 200 to remain coupled to the medial portion 280 of the stylet 255 and to move with the stylet 255 through the tissue in the direction shown by the arrow CC. Similarly, because the retention members 282 are angled toward the distal end portion 260 of the stylet 255, when the stylet 255 is moved in a direction shown by the arrow DD in FIGS. 3 and 5A, the retention members 282 do not exert a force on the medial portion 204 of the implant 200 and/or exert a force that causes the medial portion 204 to uncouple from the medial portion 280 of the stylet 255. Thus, the retention members 282 couple the medial portion 204 of the implant 200 to the stylet 255 when moved in the direction shown by the arrow CC in FIGS. 3 and 5A but do not couple the medial portion 204 of the implant 200 to the stylet 255 when moved in the direction shown by the arrow DD in FIGS. 3 and 5A.

In use, the distal end portion 202 of the implant 200 is coupled to the distal end portion 260 of the stylet 255 and the medial portion 204 of the implant 200 is coupled to the medial portion 280 of the stylet 255 via the retention members 282, as described above. The implant 200 and the stylet 255 can then be inserted into a tissue of a patient.

Figure 3:
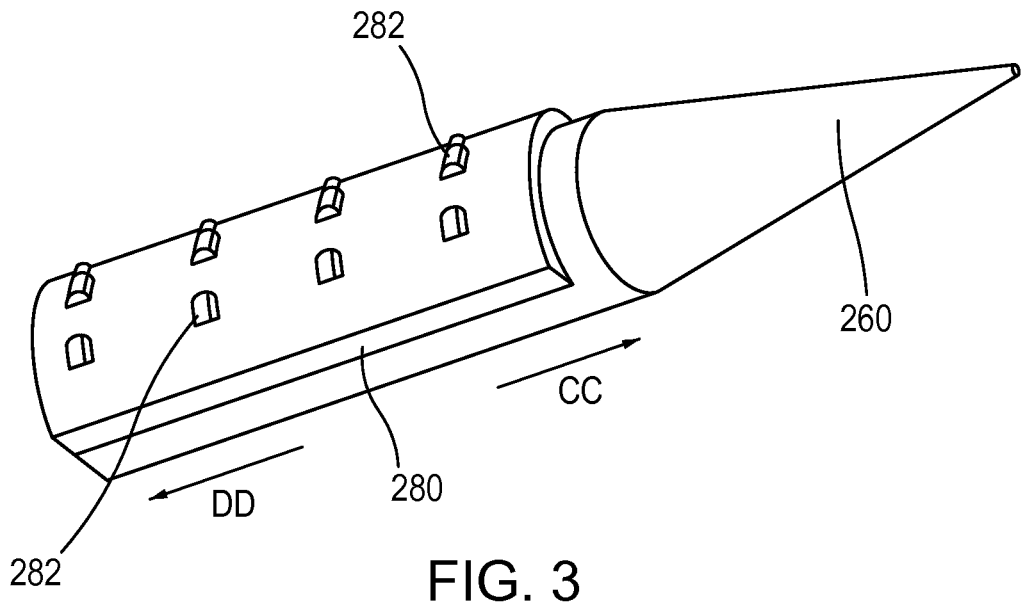
FIG. 3 is a detailed view of a portion of the insertion device of FIG. 2.
Figure 4:
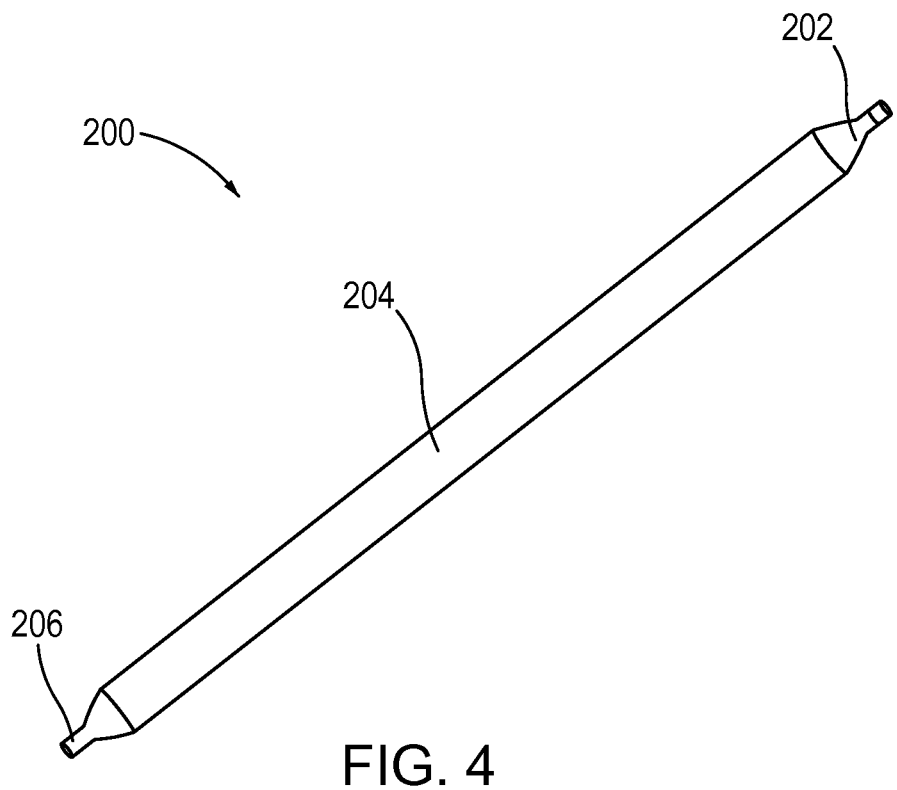
FIG. 4 is a top view of a mesh implant, according to another embodiment.

The implant 200 and the stylet 255 are inserted into the tissue of the patient in the direction shown by the arrow CC in FIGS. 3 and 5A. The distal end portion 260 of the stylet 255 penetrates and/or dilates the tissue as the stylet 255 and the implant 200 are inserted into the tissue of the patient. The distal end portion 260 of the stylet 255 and the retention members 282 of the medial portion 280 of the stylet 255 keep the implant 200 coupled to the stylet 255 as the stylet 255 and the implant 200 are moved in the direction shown by the arrow CC in FIGS. 3 and 5A.

Once the implant 200 is positioned at a desired location within the tissue, the stylet 255 is moved through the tissue in the direction shown by the arrow DD in FIGS. 3 and 5A. Moving the insertion device in the direction shown by the arrow DD uncouples distal end portion 202 of the implant 200 from the distal end portion 260 of the stylet 255 and the medial portion 204 of the implant 200 from the medial portion 280 of the stylet 255, as described above. In some embodiments, tanged portions of the implant 200 engage the tissue surrounding the implant and hold the implant 200 in place as the stylet 255 is removed from the tissue. In other embodiments, an anchor secures the implant in the tissue as the stylet is removed from the tissue.

In other embodiments, a medical practitioner uncouples the distal end portion of the implant from the distal end portion of the stylet and/or the proximal end portion of the stylet prior to removing the stylet from the tissue of the patient. In such embodiments, the movement of the stylet in the direction shown by the arrow DD in FIGS. 3 and 5A is not sufficient to uncouple the distal end portion of the implant from the distal end portion of the stylet. In some embodiments, the distal end portion of the stylet is passed through the tissue and outside a body of the patient. In other embodiments, the distal end portion of the stylet is passed through the tissue to an area within the body of the patient that the medical practitioner can access.

Figure 5B:
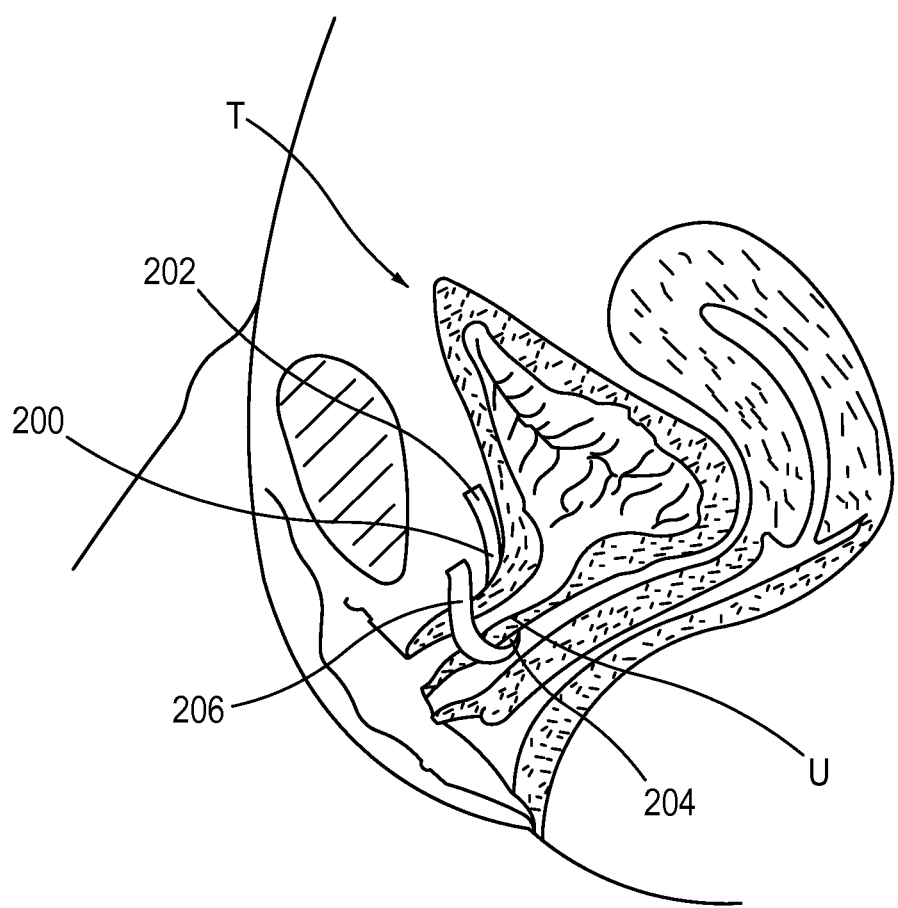
FIG. 5B shows the implant of FIG. 4 supporting a urethra of a patient.
Figure 6:
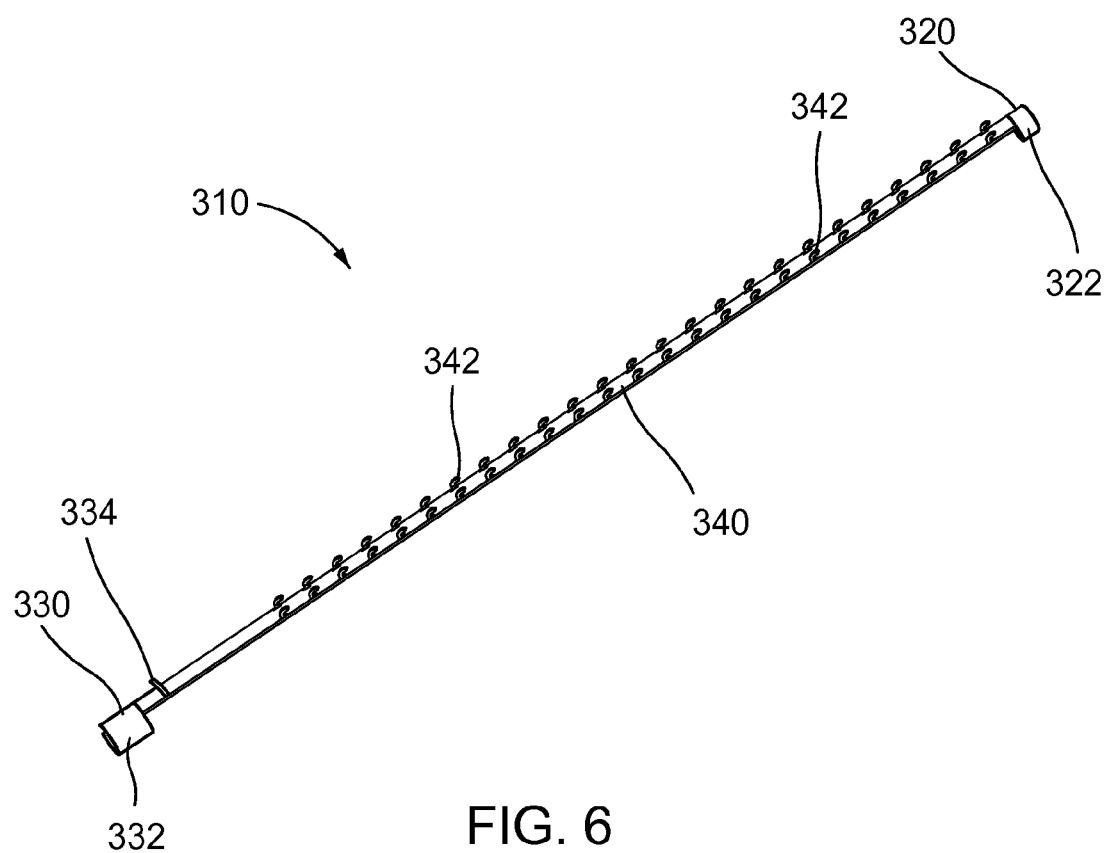
FIG. 6 is a perspective view an elongate member having a plurality of retention members, according to another embodiment.

Once the first end portion 202 of the implant 200 is disposed within the tissue of the patient, the second end portion 206 of the implant can be similarly placed within the tissue of the patient such that the medial portion 204 of the implant can support a portion of the body of the patient. FIG. 5B, for example, illustrates the implant 200 disposed within a pelvic region of the patient. The first end portion 202 of the implant 200 and the second end portion 206 of the implant 200 are disposed within a tissue T of the patient while the medial portion 204 of the implant 200 is disposed underneath and supports a urethra U of the patient.

FIGS. 6-9 show an elongate member 310 configured to be coupled to a stylet 355 to aid in inserting an implant within a tissue of a patient. The elongate member 310 includes a distal end portion 320, a proximal end portion 330 and a medial portion 340. The distal end portion 320 includes a coupling mechanism 322. Similarly, the proximal end portion 330 includes a coupling mechanism 332. The coupling mechanisms 322, 332 can be any coupling mechanisms 322, 332 configured to couple the elongate member 310 to the stylet 355 (see FIG. 8). In some embodiments, for example, the coupling mechanisms 322, 332 are clips, snaps, and/or the like. While shown as having two coupling mechanisms 322, 332, in other embodiments, the elongate member can have any number of coupling mechanisms. In some embodiments, for example, the elongate member has a single coupling mechanism. In other embodiments, the elongate member has three or more coupling mechanisms.

The elongate member 310 can conform to the shape of the stylet 355. In some embodiments, the elongate member 310 is biased in a linear configuration such that the elongate member 310 defines a straight center line (see FIG. 6) but can be bent to define a curved center line that is parallel to a center line defined by the stylet 355 (see FIG. 8). In some embodiments, the elongate member has a cross-section having an area of approximately $2*10^{-3}$ square inches.

The elongate member 310 can be constructed of any material having a high modulus of elasticity. In some embodiments, for example, the elongate member 310 is constructed of steel, nylon and/or PEEK. This causes any elongation of an implant that occurs when the implant is inserted into a tissue of a patient to be substantially equal to the elongation of the elongate member 310. Because additional elongation of the implant does not occur, the total elongation of the implant is reduced. The implant is configured to absorb the small amount of elongation that can occur.

In some embodiments, for example, an elongation of approximately 0.0125 inches per inch occurred when a tensile force of 10 lbs was applied to a nylon implant having a length of 10 inches, a modulus of elasticity of $0.4*10^6$ psi, and a cross-sectional area of $2*10^{-3}$ square inches. The implant can absorb such low levels of elongation. In other embodiments, an elongation of less than 0.0125 inches per inch occurs. For example, if a similarly sized PEEK implant having a modulus of elasticity of $3.8*10^6$ psi is used, the elongation of the implant is approximately 10 times smaller (e.g., approximately 0.00125 inches per inch). In still other embodiments, an elongation of greater than 0.0125 inches per inch occurs.

The medial portion 340 of the elongate member 310 includes multiple retention members 342. The retention members 342 are hook-shaped (see FIG. 7) and configured to receive a portion of an implant. In some embodiments, for example, each retention member 342 is configured to receive a strand of a woven or knit mesh implant. The implant is configured remain coupled to the medial portion 340 of the elongate member 310 via the retention members 342 when the elongate member 340 is moved in a direction shown by the arrow EE in FIG. 7 but uncouple from the elongate member 340 when the elongate member 340 is moved in a direction shown by the arrow FF in FIG. 7. In some embodiments, the elongate member 310 includes approximately 140 retention members 342 per 10 inches of length of the elongate member 310. In other embodiments, the elongate member includes less than 140 retention members per 10 inches of length of the elongate member. In still other embodiments, the elongate member includes greater than 140 retention members per 10 inches of length of the elongate member.

Figure 8:
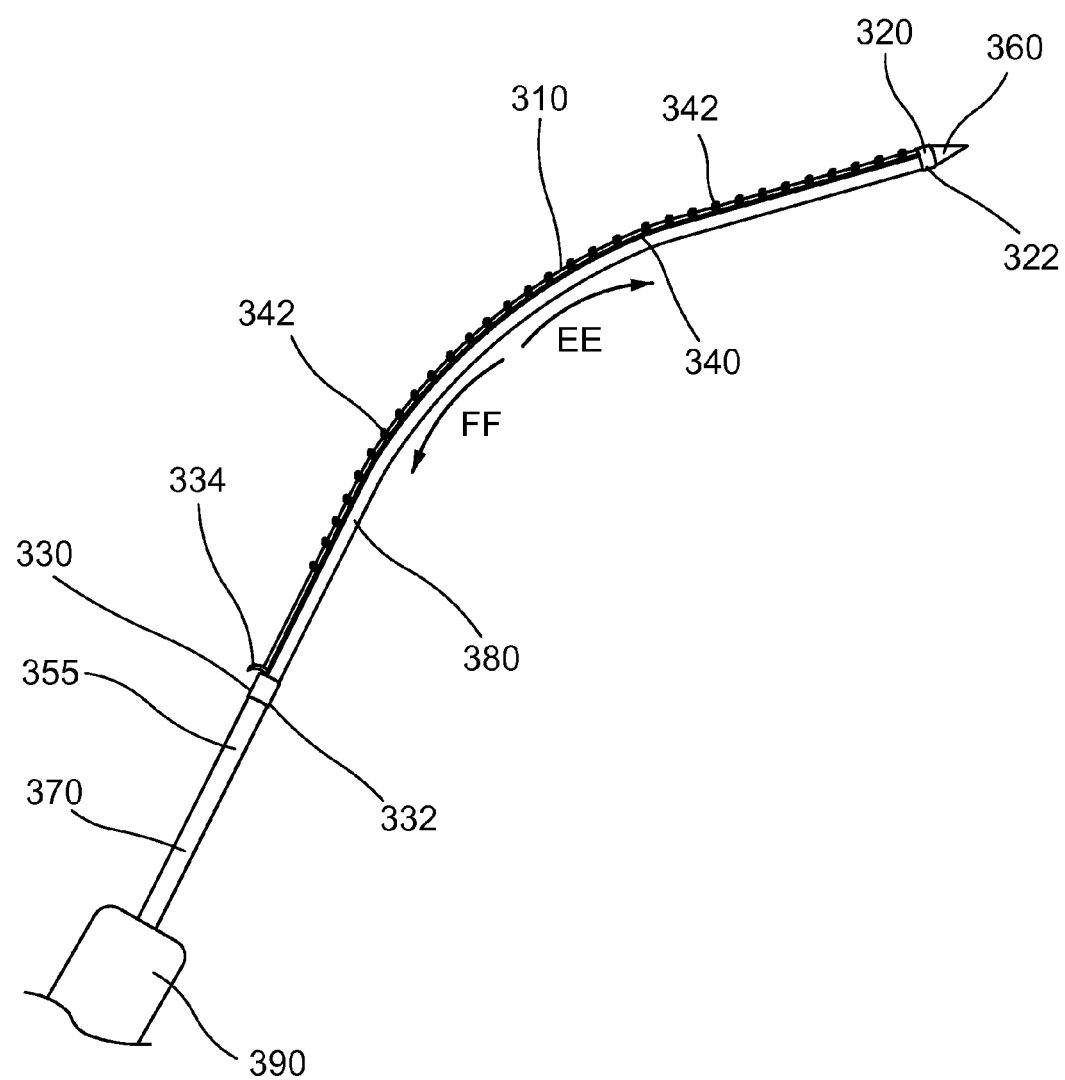
FIG. 8 is a perspective view of the elongate member of FIG. 6 coupled to an insertion device.

The retention members 342 are disposed on an opposite side of the elongate member 310 as the coupling mechanisms 322, 332. As such, when the elongate member 310 is coupled to the stylet 350, the retention members face away from the stylet 350, as shown in FIG. 8.

In some embodiments, the proximal end portion 330 of the elongate member 310 includes at least one coupler 334. The coupler 334 can be similar to the retention members 342 of the medial portion 340 of the elongate member 310. In some embodiments, the coupler 334 is hook-shaped and configured to receive a portion of the implant. In some embodiments, the coupler 334 is angled toward the proximal end of the elongate member 310 such that a free end of the coupler 334 is closer to the proximal end of the elongate member 310 than an end of the coupler 334 coupled to the elongate member 310. As such, the implant remains coupled to the proximal end portion 330 of the elongate member 210 via the coupler 334 when the medial portion 340 of the elongate member 310 is moved through a tissue in the direction shown by the arrow FF in FIGS. 7 and 8. This helps to more securely couple the implant to the elongate member 310 as the elongate member 310 and the implant are moved through a tissue. In such embodiments, a medical practitioner can uncouple the implant from the coupler 334 prior to removing the elongate member 310 from the tissue of the patient, as further described herein. In other embodiments, the retention member of the proximal end portion of the elongate member is a snap connector, an adhesive and/or the like.

The stylet 355 (see FIG. 8) includes a proximal end portion 370, a distal end portion 360 and a medial portion 380 between the distal end portion 360 and the proximal end portion 370. The stylet 355 is curved. This allows a medical practitioner to insert an implant 300 into difficult to reach tissues. For example, the curved stylet 355 allows a medical practitioner to maneuver around a portion of a body of a patient and insert the implant 300 into tissue obstructed by the portion of the body. In other embodiments, the stylet is straight.

The proximal end portion 370 of the stylet 355 is coupled to a handle 390. A medical practitioner can use the handle 390 to control and/or guide the stylet 355 when inserting the stylet 355 into a body of a patient.

Similar to the stylet 255, the distal end portion 360 of the stylet 355 is configured to be coupled to a distal end portion of an implant to be inserted into a tissue of a patient. In some embodiments, the distal end portion of the implant defines a lumen configured to receive the distal end portion 360 of the stylet 355. The distal end portion 360 of the stylet 355 is tapered such that the distal end portion 360 is configured to pierce and/or dilate a tissue as the stylet 355 is inserted into the tissue. A portion of the distal end portion 360 of the stylet 355 with the largest cross-section (e.g., diameter), has a cross-section larger than the lumen defined by the distal end portion of the implant. Accordingly, the distal end portion of the implant remains coupled to the stylet 355 when the stylet 355 is moved in a direction shown by the arrow EE in FIG. 8, but uncouples from the stylet 355 when the stylet 355 is moved in a direction shown by the arrow FF in FIG. 8.

In other embodiments, the distal end portion of the implant is coupled to the distal end portion of the elongate member. In some embodiments, for example, the distal end portion of the implant is fixedly coupled to the distal end portion of the elongate member and a medical practitioner breaks the coupling of the distal end portion of the implant and the distal end portion of the elongate member before removing the elongate member from the tissue of the patient, as further described herein. In yet other embodiments, the distal end portion of the implant is releasably coupled to the distal end portion of the elongate member by a clip, a snap, and/or the like.

In use, the elongate member 310 is coupled to the stylet 355 by the coupling mechanisms 322, 332. The elongate member 310 flexes to conform to the curved shape of the stylet 355. An implant is then coupled to the elongate member 310 and the stylet 355. Specifically, a distal end portion of the implant is coupled to the distal end portion 360 of the stylet 355 and a medial portion of the implant is coupled to the medial portion 340 of the elongate member 310 via the retention members 342. In some embodiments, the implant is also coupled to the proximal end portion 330 of the elongate member 310 via the coupler 334, as described above. The implant can be structurally and functionally similar to the implant 200, shown and described above.

Figure 7:
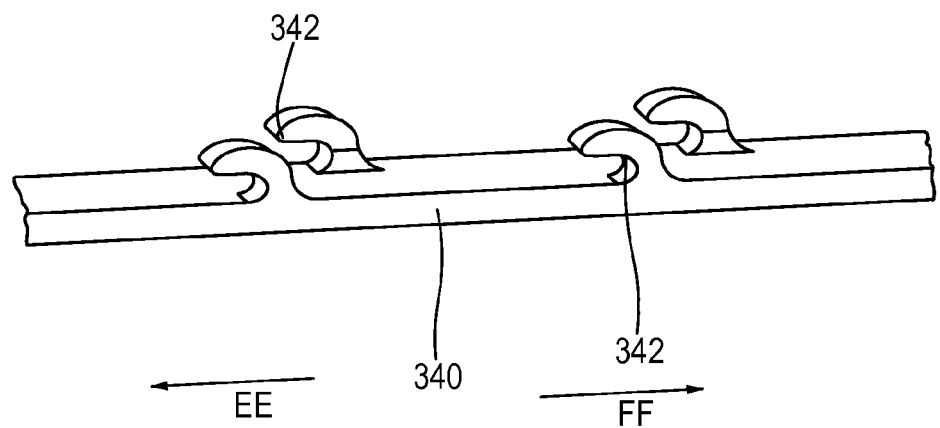
FIG. 7 is a detailed perspective view of a portion of the elongate member of FIG. 6.

The implant, stylet 355 and the elongate member 310 are inserted into the tissue of the patient in the direction shown by the arrow EE in FIGS. 7 and 8. When moved in the direction shown by the arrow EE in FIGS. 7 and 8, the force applied to the implant is distributed among the retention members 342, causing less elongation of the implant at any one portion of the implant than would occur with a single retention member. In some embodiments, the average load per hook is approximately 0.07 lbs.

The distal end portion 360 of the stylet 355 penetrates and dilates the tissue as the stylet 355, implant and elongate member 310 are inserted into the tissue of the patient. The distal end portion 360 of the stylet 355 and the retention members 342 of the medial portion 340 of the elongate member 310 keep the implant 300 coupled to the stylet 355 as the stylet 355, implant and elongate member 310 are moved through the tissue in the direction shown by the arrow EE in FIGS. 7 and 8. In some embodiments, the coupler 334 of the proximal end portion 330 of the elongate member 310 also assists in keeping the implant 300 coupled to the stylet 335, as described above.

In some embodiments, once the implant is positioned at a desired location within the tissue, a medical practitioner uncouples the implant from the coupler 334 by unhooking the implant, cutting a portion of the implant, unsnapping the implant, and/or the like. The stylet 355 and the elongate member 310 are moved through the tissue in the direction shown by the arrow FF in FIGS. 7 and 8. Moving the stylet 355 and the elongate member 310 in the direction shown by the arrow FF uncouples distal end portion of the implant from the distal end portion 360 of the stylet 355 and the medial portion of the implant from the medial portion 340 of the elongate member 310, as described above. In some embodiments, tanged portions of the implant are used to engage the tissue and retain the implant in place as the stylet and the elongate member are removed from the tissue. In other embodiments, an anchor secures the implant with respect to the tissue as the stylet and the elongate member are removed from the tissue. Once the first end portion of the implant is disposed within the tissue of the patient, the second end portion of the implant can be similarly placed within the tissue of the patient such that the medial portion of the implant can support a portion of the body of the patient.

Figure 9:
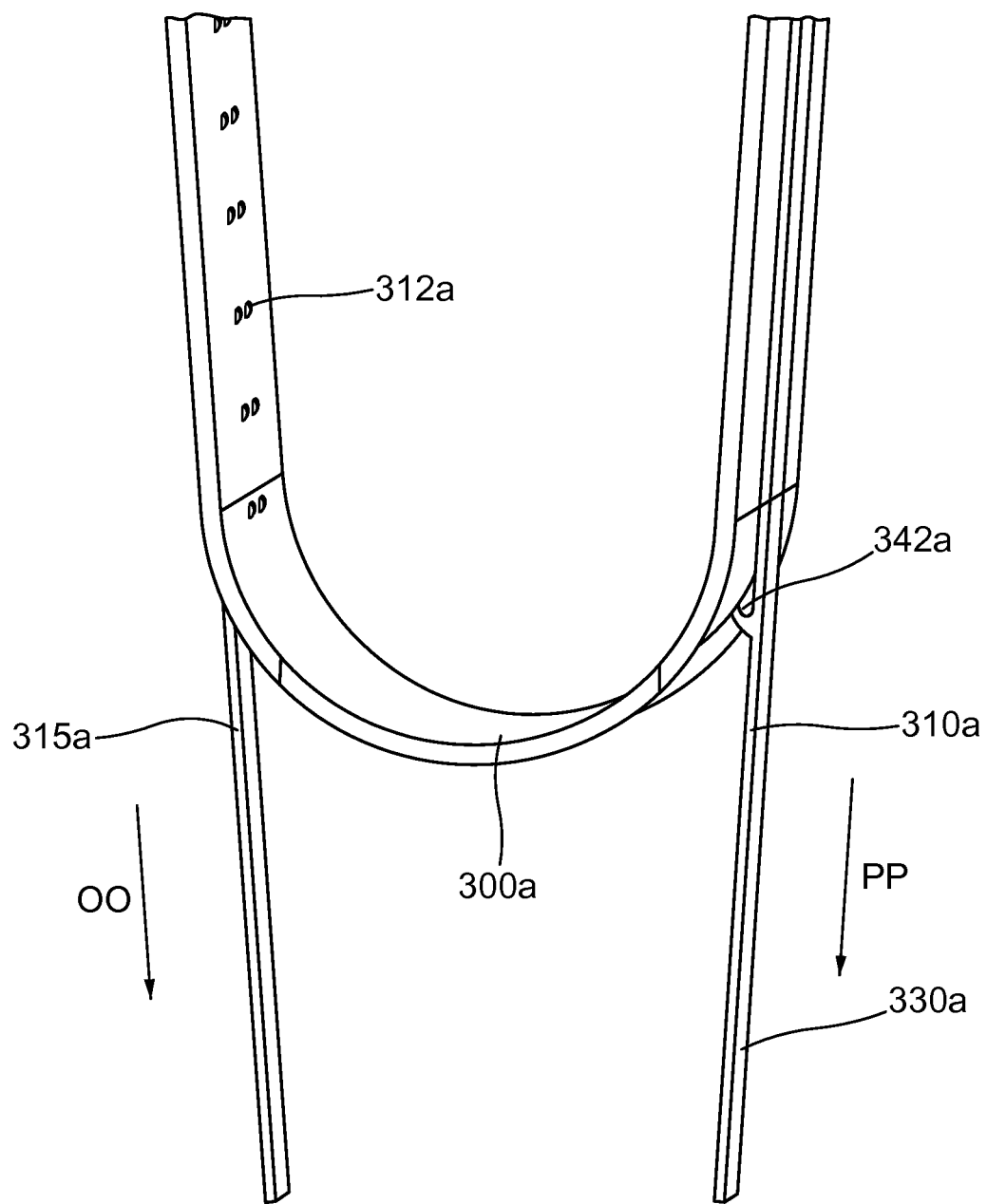
FIG. 9 is a perspective view of two elongate members and an implant, according to another embodiment.

In other embodiments, the stylet is removed from the tissue of the patient separately from the elongate member. In some embodiments, for example, once the implant is positioned at a desired location within the tissue and the distal end portion of the stylet has passed through the tissue such that the distal end portion of the stylet is accessible to a medical practitioner, the medical practitioner can uncouple the implant and the elongate member from the stylet. In some embodiments, the distal end portion of the stylet is passed through the tissue and outside a body of the patient. In other embodiments, the distal end portion of the stylet is passed through the tissue to an area within the body of the patient that the medical practitioner can access. Specifically, the medical practitioner can uncouple the distal end portion of the implant from the distal end portion of the stylet, the coupling mechanism of the distal end portion of the elongate member from the stylet, and the coupling mechanism of the proximal end portion of the elongate member from the stylet. The stylet can then be removed from the tissue of the patient while leaving the elongate member and the implant within the tissue of the patient. For example, the stylet can be removed by moving the stylet in a direction shown by the arrow FF in FIGS. 7 and 8. The medical practitioner can then use the elongate member to further position the implant in the tissue of the patient. Once the implant is correctly positioned within the tissue of the patient, the elongate member can be removed from the tissue of the patient. FIG. 9 shows an implant 300a having a first end portion and a second end portion disposed within a tissue of a patient. A first elongate member 315a and a second elongate member 330a are still coupled to the implant 300a via retention members 312a and 342a, respectively. The first elongate member 315a and the second elongate member 330a can be uncoupled from the implant and removed from the tissue of the patient by being moved in directions shown by the arrows OO and PP in FIG. 9, respectively.

In some embodiments, if the proximal end portion of the elongate member has a retention member, the medical practitioner uncouples the implant from the retention member of the proximal end portion of the elongate member prior to removing the elongate member from the tissue of the patient. Similarly, in embodiments where the distal end portion of the implant is coupled to the distal end portion of the elongate member, the distal end portion of the implant is uncoupled from the distal end portion of the elongate member prior to removing the elongate member from the tissue of the patient.

FIG. 10 shows an elongate member 410 configured to be coupled to a stylet 450, according to another embodiment. The elongate member 410 includes a distal end portion 420, a proximal end portion 430 and a medial portion 440. The distal end portion 420 includes a coupling mechanism 422. Similarly, the proximal end portion 430 includes a coupling mechanism 432. The coupling mechanisms 422, 432 can be any coupling mechanisms 422, 432 configured to couple the elongate member 410 to the stylet 455 (see FIG. 11). In some embodiments, for example, the coupling mechanisms 422, 432 are clips, snaps, and/or the like. While shown as having two coupling mechanisms 422, 432, in other embodiments, the elongate member can have any number of coupling mechanisms. In some embodiments, for example, the elongate member has a single coupling mechanism. In other embodiments, the elongate member has three or more coupling mechanisms.

The elongate member 410 is constructed of a flexible material, such that it can conform to the shape of the stylet 455. In some embodiments, the elongate member 410 is biased to define a straight center line (see FIG. 10) but can be bent to define a curved center line that is parallel to a center line defined by the stylet 455 (see FIG. 11).

The medial portion 440 of the elongate member 410 includes multiple retention members 442. The retention members 442 are disposed on a same side of the elongate member 410 as the coupling mechanisms 422, 432. As such, when the elongate member 410 is coupled to the stylet 455, the retention members face or extend toward the stylet 455, as shown in FIG. 11 and the implant 400 is disposed between the elongate member 410 and the stylet 455. In some embodiments, the retention members 442 contact the stylet 455 when the elongate member 410 is coupled to the stylet.

In some embodiments, the proximal end portion 430 of the elongate member 410 includes couplers 434. The couplers 434 are similar to the retention members 442 of the medial portion 440 of the elongate member 410. In some embodiments, the couplers 434 are hook-shaped and configured to receive a portion of the implant 400. In some embodiments, the couplers 334 are angled toward the proximal end of the elongate member 410 such that a free end of each coupler 434 is closer to the proximal end of the elongate member 410 than an end of the coupler 434 coupled to the elongate member 410. As such, the implant 400 remains coupled to the proximal end portion 430 of the elongate member 410 via the couplers 334 when the medial portion 440 of the elongate member 410 is moved through a tissue in the direction shown by the arrow HH in FIG. 12. This helps to securely couple the implant 400 to the elongate member 410 as the elongate member 410 and the implant 400 are moved through a tissue. In such embodiments, a medical practitioner can uncouple the implant 400 from the couplers 434 prior to removing the elongate member 410 from the tissue of the patient, as further described herein. In other embodiments, the retention members of the proximal end portion of the elongate member are snap connectors, an adhesives, staples and/or the like.

The stylet 455 (see FIG. 11) includes a proximal end portion 470, a distal end portion 460 and a medial portion 480 between the distal end portion 460 and the proximal end portion 470. The stylet 455 is substantially similar to the stylet 355 shown and described above.

The proximal end portion 470 of the stylet 455 is coupled to a handle 490. A medical practitioner can use the handle 490 to control and/or guide the stylet 455 when inserting the stylet 455 into a body of a patient.

Figure 12:
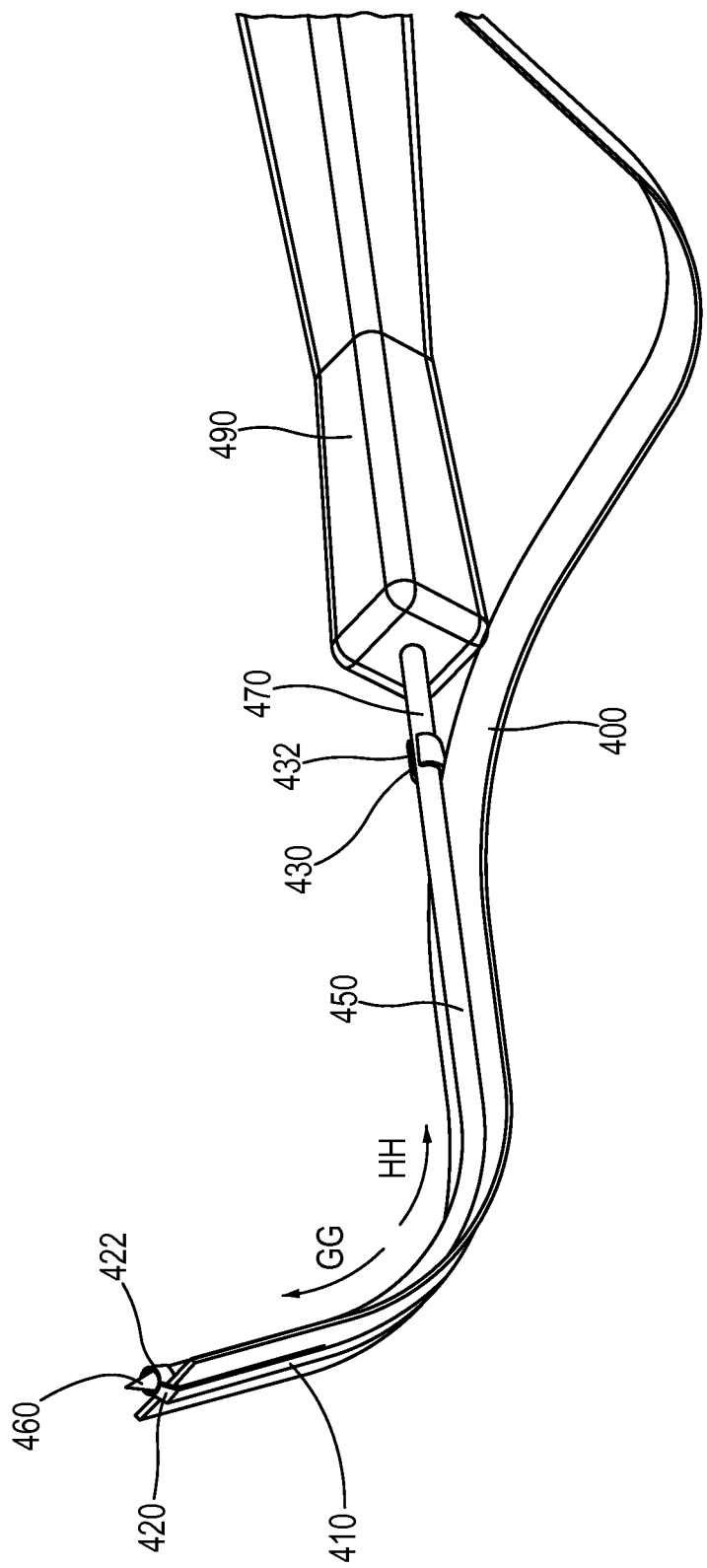
FIG. 12 is a perspective view of an implant and an insertion device, according to another embodiment.

In use, an implant 400 is positioned on the stylet 450 and the elongate member 410 is coupled to the stylet 455 by the coupling mechanisms 422, 432. This sandwiches or couples the implant 400 between the elongate member and the stylet 455, as shown in FIG. 12. The elongate member 410 flexes to conform to the curved shape of the stylet 455. The implant 400 can be structurally and functionally similar to the implant 200, shown and described above.

The implant, stylet 455 and the elongate member 410 are inserted into the tissue of the patient in the direction shown by the arrow GG in FIG. 12. The distal end portion 460 of the stylet 455 penetrates and/or dilates the tissue as the stylet 455, implant 400 and elongate member 410 are inserted into the tissue of the patient. The retention members 442 of the medial portion 440 of the elongate member 410 keep the implant 400 coupled to the elongate member 410 as the stylet 455, implant and elongate member 410 are moved through the tissue in the direction shown by the arrow GG in FIG. 12.

Positioning the implant 400 between the elongate member 410 and the stylet 450 during insertion may better secure the implant 400 to the stylet 450 and provides additional protection for the implant 400. For example, because the implant is disposed between the elongate member 410 and the stylet 450, the elongate member 410, securely holds the implant in place against the stylet 450. Further, there is less of a risk that the implant 400 might come uncoupled from the stylet 450, causing the implant 400 to be improperly placed.

Once the implant 400 is positioned at a desired location within the tissue and the distal end portion 460 of the stylet 450 has passed through the tissue such that the distal end portion 460 of the stylet 450 is disposed outside the tissue and is accessible to a medical practitioner, the medical practitioner can uncouple the implant 400 and the elongate member 410 from the stylet 450. In some embodiments, for example, the distal end portion 460 of the stylet 450 is passed through the tissue and outside a body of the patient. In other embodiments, the distal end portion of the stylet is passed through the tissue to an area within the body of the patient that the medical practitioner can access. The medical practitioner can uncouple the coupling mechanism 422 of the distal end portion 420 of the elongate member 410 and the coupling mechanism 432 of the proximal end portion 430 of the elongate member 410 from the stylet 450. The stylet 450 can then be removed from the tissue of the patient by moving the stylet through the tissue in a direction shown by the arrow HH in FIG. 8. The medical practitioner can then use the elongate member 410 to further position the implant 400 in the tissue of the patient. Once the implant 400 is correctly positioned within the tissue of the patient, the elongate member 410 can be removed from the tissue of the patient by moving the elongate member 410 in a direction shown by the arrow HH in FIG. 12. In some embodiments, tanged portions of the implant 400 help maintain the position of the implant 400 in the tissue of the patient while the elongate member 410 is removed from the tissue.

In some embodiments, the medical practitioner uncouples the implant from the retention member of the proximal end portion of the elongate member prior to removing the elongate member from the tissue of the patient. Similarly, in embodiments where the distal end portion of the implant is coupled to the distal end portion of the elongate member, the distal end portion of the implant is uncoupled from the distal end portion of the elongate member prior to removing the elongate member from the tissue of the patient.

Once the first end portion of the implant is disposed within the tissue of the patient, the second end portion of the implant can be similarly placed within the tissue of the patient such that the medial portion of the implant can support a portion of the body of the patient.

FIG. 13 shows an elongate member 510 having a first portion 534 and a second portion 522, according to another embodiment. The first portion 534 is coupled to the second portion 522 via a coupling member 540. The coupling member 540 can be anything configured to couple a first portion 534 with a second portion 522. In some embodiments, for example, the coupling member 540 is a string, a rod, a snap, an adhesive and/or the like. In other embodiments, the first portion of the elongate member, the second portion of the elongate member and the coupling member are monolithically formed.

The first portion 534 includes multiple retention members 542. The retention members 542 can be similar to the retention members shown and described above. Accordingly, the retention members 542 are configured to releasably couple an implant to the first portion of the elongate member 510.

The second portion 522 of the elongate member 510 is a dilator. The second portion 522 of the elongate member 510 is configured to be inserted into a tissue of a patient prior to the first portion 534 being inserted into the tissue of the patient. The second portion 522 of the elongate member 510 is configured to dilate and/or prepare the tissue to receive an implant.

The second portion 522 of the elongate member 510 defines a lumen 524. The lumen 524 is configured to receive at least a portion of a stylet 555, as further described herein. The second portion 522 of the elongate member 510 can be constructed of any biocompatible material suitable to form a taper.

In use, the stylet 555 is inserted into the lumen 524 defined by the second portion 522 of the elongate member 510 such that the second portion 522 of the elongate member 510 is disposed on the stylet 555 between a distal end portion 560 of the stylet 555 and a proximal end portion 570 of the stylet 555, as shown in FIG. 14.

An implant is coupled to the first portion 534 of the elongate member 510. The implant can be substantially similar to the implant 200, shown and described herein. The implant is coupled to the first portion 534 of the elongate member 510 via the retention members 542. In some embodiments, a distal end portion of the implant is also coupled to a distal end portion 536 of the first portion 534 of the elongate member 510. In such embodiments, the distal end portion of the implant can be coupled to the distal end portion 536 of the first portion 534 of the elongate member 510 using an adhesive, a glue, a snap connector, hooks and/or the like. This helps stabilize the implant as it is inserted into the tissue of the patient.

The stylet 555 and the second portion 522 of the elongate member 510 are inserted into the tissue of the patient in the direction shown by the arrow II in FIG. 14. The distal end portion 560 of the stylet 555 penetrates the tissue and the second portion 522 of the elongate member 510 dilates the tissue as the stylet 555 and the second portion 522 of the elongate member 510 are inserted into the tissue of the patient. The stylet 555 and the second portion 522 of the elongate member 510 are inserted such that the distal end portion 560 of the stylet 555 and a distal end portion 520 of the second portion 522 of the elongate member 510 extend through the tissue and are accessible to a medical practitioner. In some embodiments, the distal end portion 520 of the second portion 522 of the elongate member 510 is passed through the tissue and outside a body of the patient. In other embodiments, the distal end portion of the second portion of the elongate member is passed through the tissue to an area within the body of the patient that the medical practitioner can access.

The medical practitioner holds the distal end portion 520 of the second portion 522 of the elongate member 510 as the stylet 555 is pulled in the direction shown by the arrow JJ in FIG. 14. The distal end portion 560 of the stylet 510 passes through the lumen 524 of the second portion 522 of the elongate member 510 and out of the body of the patient. This removes the stylet 555 from the tissue of the patent while leaving at least a portion of the elongate member 510 in the tissue.

The second portion 522 of the elongate member 510 is pulled by the medical practitioner in a direction shown by the arrow II in FIG. 14. This pulls the second portion 522 through the tissue and pulls the first portion 534 of the elongate member 510 and the implant coupled to the first portion 534 into the tissue. The retention members 542 of the first portion 534 of the elongate member 510 keep the implant 500 coupled to the first portion 534 of the elongate member 510 as the implant and the first portion 534 of the elongate member 510 are moved through the tissue in the direction shown by the arrow II in FIG. 14.

Once the implant 500 is positioned at a desired location within the tissue and the coupling member 540 of the elongate member 510 has passed through the tissue such that the coupling member 540 of the elongate member 510 is accessible to a medical practitioner, the medical practitioner can uncouple the second portion 522 of the elongate member 510 from the first portion 534 of the elongate member 510. In some embodiments, if a distal end portion of the implant is coupled to the distal end portion 536 of the first portion 534 of the elongate member 510, the medical practitioner can uncouple the implant from the distal end portion 536. In such embodiments, this can be done by removing the distal end portion 536 of the first portion 534 from the elongate member 510 (e.g., cutting the distal end portion 536 of the first portion 534 off of the elongate member 510), removing the distal end portion of the implant from the implant (e.g., cutting the distal end portion of the implant off of the implant), unsnapping a snap-connector, unhooking a hook and/or the like. The second portion 522 of the elongate member 510, the coupling member 540 of the elongate member 510 and any portion of the implant and the first portion 542 of the elongate member 510 removed from the first portion 542 of the elongate member 510 can be removed from the body of the patient.

The medical practitioner can then use the first portion 534 of the elongate member 510 to further position the implant 500 in the tissue of the patient. Once the implant 500 is correctly positioned within the tissue of the patient, the first portion 534 of the elongate member 510 can be removed from the tissue of the patient by moving (e.g., pulling) the first portion 534 of the elongate member 510 in a direction shown by the arrow JJ in FIG. 14. By moving the first portion 534 of the elongate member 510 in the direction shown by the arrow JJ in FIG. 14, the retention members 542 do not engage the implant. In some embodiments, tanged portions of the implant 500 maintain the position of the implant 500 in the tissue of the patient while the first portion 534 of the elongate member 510 is removed from the tissue.

Once the first end portion of the implant is disposed within the tissue of the patient, a second end portion of the implant can be similarly placed within the tissue of the patient such that the medial portion of the implant can support a portion of the body of the patient.

FIG. 15 shows an elongate member 610 having multiple retention members 642, according to another embodiment. The elongate member includes a first end portion 620, a second end portion 630 and a medial portion 640 between the first end portion 620 and the second end portion 630. The first end portion 620 defines an aperture 622 configured to be coupled to a stylet 550, as further described herein. In other embodiments, the first end portion includes any other suitable coupling mechanism, such as, for example, a snap connector, an adhesive, a staple, a tie, and/or the like.

In some embodiments, a first end portion 602 of an implant 600 is configured to be coupled to the first end portion 620 of the elongate member 610. In such embodiments, the first end portion 602 of the implant 600 can be coupled to the first end portion 620 of the elongate member 610 using an adhesive, a glue, a snap connector, hooks and/or the like.

The medial portion 640 of the elongate member 610 includes multiple retention members 642. The retention members 642 are configured to releasably couple a portion of an implant 600 to the medial portion 640 of the elongate member 610. In some embodiments, the retention members 642 are hooks. In such embodiments, the hooks are configured to be inserted into apertures defined by the implant 600. In some embodiments, the apertures defined by the implant 600 can be defined by the woven or knitted mesh of the implant 600. The retention members 642 are configured to retain the implant 600 when the elongate member 610 is moved substantially in a direction shown by the arrow KK in FIG. 16 but release the implant 600 when the elongate member 610 is moved substantially in a direction shown by the arrow LL in FIG. 16.

In some embodiments, the second end portion 630 of the elongate member 610 includes couplers 634. The couplers 634 can be similar to the retention members 642 of the medial portion 640 of the elongate member 610. In some embodiments, the couplers 634 are hook-shaped and configured to receive a portion of the implant 600. In some embodiments, the couplers 634 are angled toward the proximal end of the elongate member 610 such that a free end of each coupler 634 is closer to the proximal end of the elongate member 610 than an end of each coupler 634 coupled to the elongate member 610. As such, the implant 600 remains coupled to the second end portion 630 of the elongate member 610 via the coupler 634 when the medial portion 640 of the elongate member 610 is moved through a tissue in the direction shown by the arrow GG in FIG. 12. This helps to securely couple the implant 600 to the elongate member 610 as the elongate member 610 and the implant 600 are moved through a tissue. In such embodiments, a medical practitioner can uncouple the implant 600 from the couplers 634 prior to removing the elongate member 610 from the tissue of the patient, as further described herein. In other embodiments, the retention members of the second end portion of the elongate member are snap connectors, adhesives and/or the like.

FIG. 16 shows the elongate member 610 coupled to an implant 600 and a distal end portion 660 of a stylet 650. The implant 600 can be similar to the implants shown and described above. The distal end portion of the stylet 650 defines a coupling mechanism 662 configured to couple the first end portion 620 of the elongate member 610 to the stylet 650. In some embodiments, the aperture 622 is configured to receive a portion of the coupling mechanism 662. The coupling mechanism 662 can be a hook, a notch, and/or the like. In other embodiments, the coupling mechanism can be a snap, a suture, and/or any other type of coupling mechanism.

In use, the stylet 650 is inserted through a tissue of a patient in a direction shown by the arrow LL in FIG. 16 such that the distal end portion 660 of the stylet 650 passes entirely through the tissue and a medical practitioner has access to the distal end portion 660 of the stylet 650. In some embodiments, the distal end portion 660 of the stylet 650 is passed through the tissue and outside a body of the patient. In other embodiments, the distal end portion of the stylet is passed through the tissue to an area within the body of the patient that the medical practitioner can access. The implant 600 is coupled to the elongate member 610 via the retention members 642.

The first end portion 620 of the elongate member 610 is then coupled to the distal end portion 660 of the stylet 650. Specifically, the aperture 622 defined by the first end portion 620 of the elongate member 610 receives the coupling mechanism 662. The stylet 650 is then moved through the tissue in a direction shown by the arrow KK in FIG. 16. This causes the stylet 650 to pull the elongate member 610 and the implant 600 into the tissue of the patient.

Once the implant 600 is positioned within the tissue of the patient and the first end portion 620 of the elongate member 610 and the distal end portion 660 of the sylet 650 are disposed outside the tissue of the patient, the medical practitioner can uncouple the first end portion 620 of the elongate member 610 from the distal end portion 660 of the stylet 650.

The medical practitioner can then use the elongate member 610 to further position the implant 600 (e.g., fine tune the position of the implant 600) in the tissue of the patient by moving the elongate member 610 in the direction shown by the arrow KK in FIG. 16. Once the implant 600 is correctly positioned within the tissue of the patient, the elongate member 610 can be removed from the tissue of the patient by moving the elongate member 610 in a direction shown by the arrow LL in FIG. 16. In some embodiments, tanged portions of the implant 600 maintain the position of the implant 600 in the tissue of the patient while the elongate member 610 is removed from the tissue.

Once the first end portion 602 of the implant 600 is disposed within the tissue of the patient, a second end portion (not shown) of the implant 600 can be similarly placed within the tissue of the patient such that the medial portion of the implant 600 can support a portion of the body of the patient.

Figure 17:
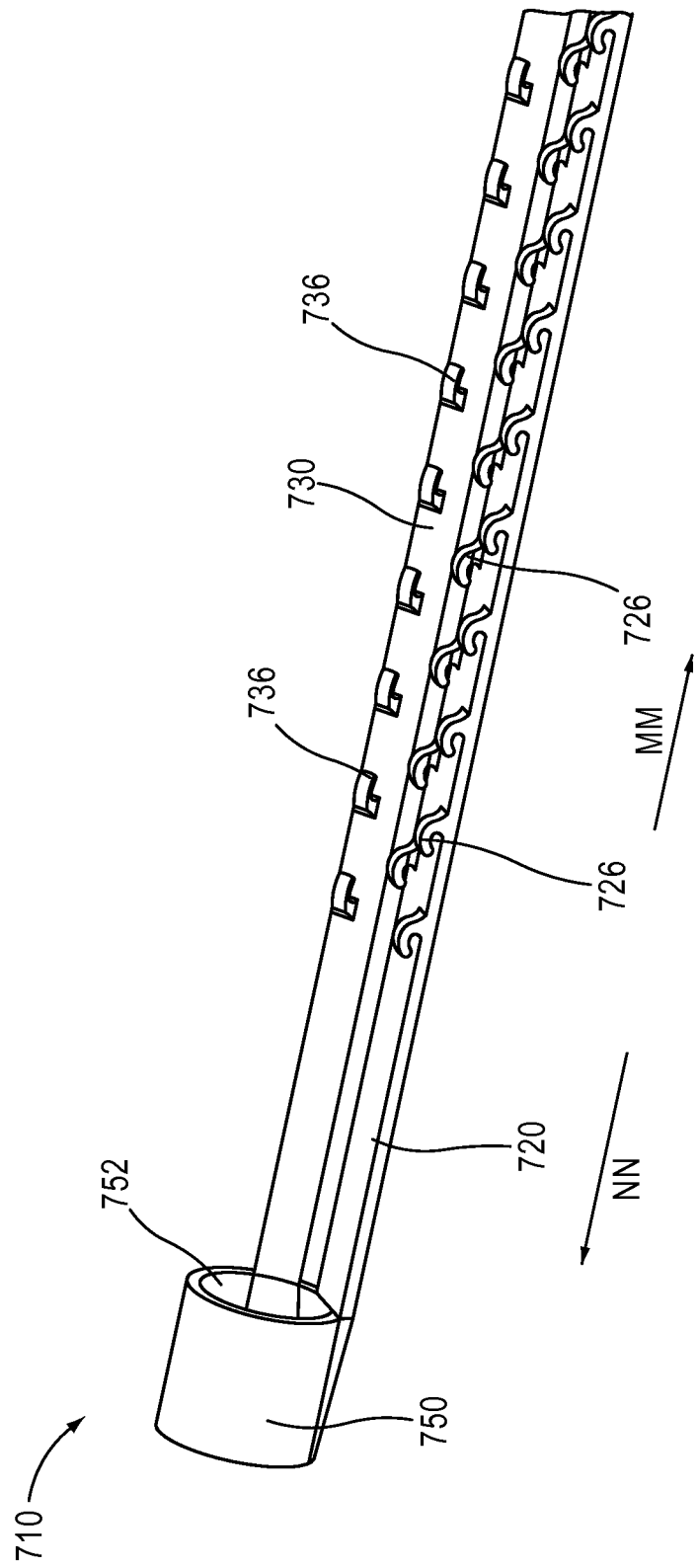
FIG. 17 is a perspective view a first elongate member having a plurality of retention members and a second elongate member having a plurality of retention members, according to another embodiment.

FIG. 17 shows a portion of a insertion device 710 having a first elongate member 720 and a second elongate member 730. The first elongate member 720 and the second elongate member 730 are coupled to each other at an end portion 750 of the insertion device 710. The end portion 750 of the insertion device 710 defines a lumen 752 configured to receive a portion of a stylet (not shown). The insertion device 710 is configured to be coupled to the stylet via the lumen 752.

The first elongate member 720 includes multiple retention members 726. As shown in FIG. 17, the retention members 726 are angled toward the end portion 750 of the insertion device 710 such that a free end of each retention member 726 is closer to the end portion 750 of the insertion device 710 than an end of each retention member 726 coupled to the second elongate member. The retention members 726 are hook-shaped and configured to receive a portion of an implant. In some embodiments, for example, each retention member 726 is configured to receive a strand of a woven or knitted mesh implant. The implant is configured remain coupled to the first elongate member 720 via the retention members 726 when the first elongate member 720 is moved in a direction shown by the arrow NN in FIG. 17 but uncouple from the first elongate member 720 when the first elongate member 720 is moved in a direction shown by the arrow MM in FIG. 17.

Similarly, the second elongate member 730 includes multiple retention members 736. As shown in FIG. 17, the retention members 736 are angled away from the end portion 750 of the insertion device 710 such that a free end of each retention member 736 is further away to the end portion 750 of the insertion device 710 than an end of each retention member 736 coupled to the second elongate member. The retention members 736 are hook-shaped and configured to receive a portion of an implant. In some embodiments, for example, each retention member 736 is configured to receive a strand of a woven or knitted mesh implant. The implant is configured remain coupled to the second elongate member 730 via the retention members 736 when the second elongate member 730 is moved in a direction shown by the arrow MM in FIG. 17 but uncouple from the second elongate member 730 when the second elongate member 730 is moved in a direction shown by the arrow NN in FIG. 17.

In use, an implant (not shown) is coupled to the first elongate member 720 and the second elongate member 730 of the insertion device 710 via the retention members 726 and the retention members 736, respectively. In other embodiments, the implant is also coupled to end portions of the insertion device, similar to the embodiments shown and described above.

The insertion device 710 is coupled to a stylet. The insertion device 710, the stylet and the implant can then be inserted into a tissue of a patient. Once the implant is disposed within the tissue and a distal end portion of the insertion device 710 is passed through the tissue, the insertion device 710 is uncoupled from the stylet (e.g., cut, unsnapped, removed, and/or the like) and the stylet is removed from the tissue of the patient. The insertion device 710 can then be used to further position the implant in the tissue of the patient. Specifically, if the implant needs to be moved further in the direction shown by the arrow NN in FIG. 17, the implant remains coupled to the insertion device 710 via the retention members 726 of the first elongate member 720. Similarly, if the implant needs to be moved further in the direction shown by the arrow MM in FIG. 17, the implant remains coupled to the insertion device 710 via the retention members 736 of the second elongate member 720. Accordingly, having elongate members 720, 730 with retention members 726, 736 facing opposite directions allows a medical practitioner to adjust the position of the implant within the tissue in both directions without the implant uncoupling from the insertion device 710.

Once the implant is disposed at the desired location within the tissue of the patient, the first elongate member 720 can be uncoupled from the second elongate member 730 by the medical practitioner. The first elongate member 720 can then be removed from the tissue of the patient by pulling the first elongate member 720 through the tissue in the direction shown by the arrow MM in FIG. 17. When moved in this direction, the retention members 726 uncouple from the implant leaving the implant disposed at the desired location within the tissue of the patient. Similarly, the second elongate member 730 can then be removed from the tissue of the patient by pulling the second elongate member 730 through the tissue in the direction shown by the arrow NN in FIG. 17. When moved in this direction, the retention members 736 uncouple from the implant leaving the implant disposed at the desired location within the tissue of the patient.

In embodiments where the implant is coupled to end portions of the insertion device, a medical practitioner can uncouple the implant from the end portions of the insertion device before removing the first elongate member and the second elongate member from the tissue of the patient. In such embodiments, this can be done by removing the end portion of the insertion device from the insertion device (e.g., cutting the end portion of the insertion device off of the insertion device), removing the end portion of the implant from the implant (e.g., cutting the end portion of the implant off of the implant), unsnapping a snap-connector, unhooking a hook and/or the like.

Figure 18:
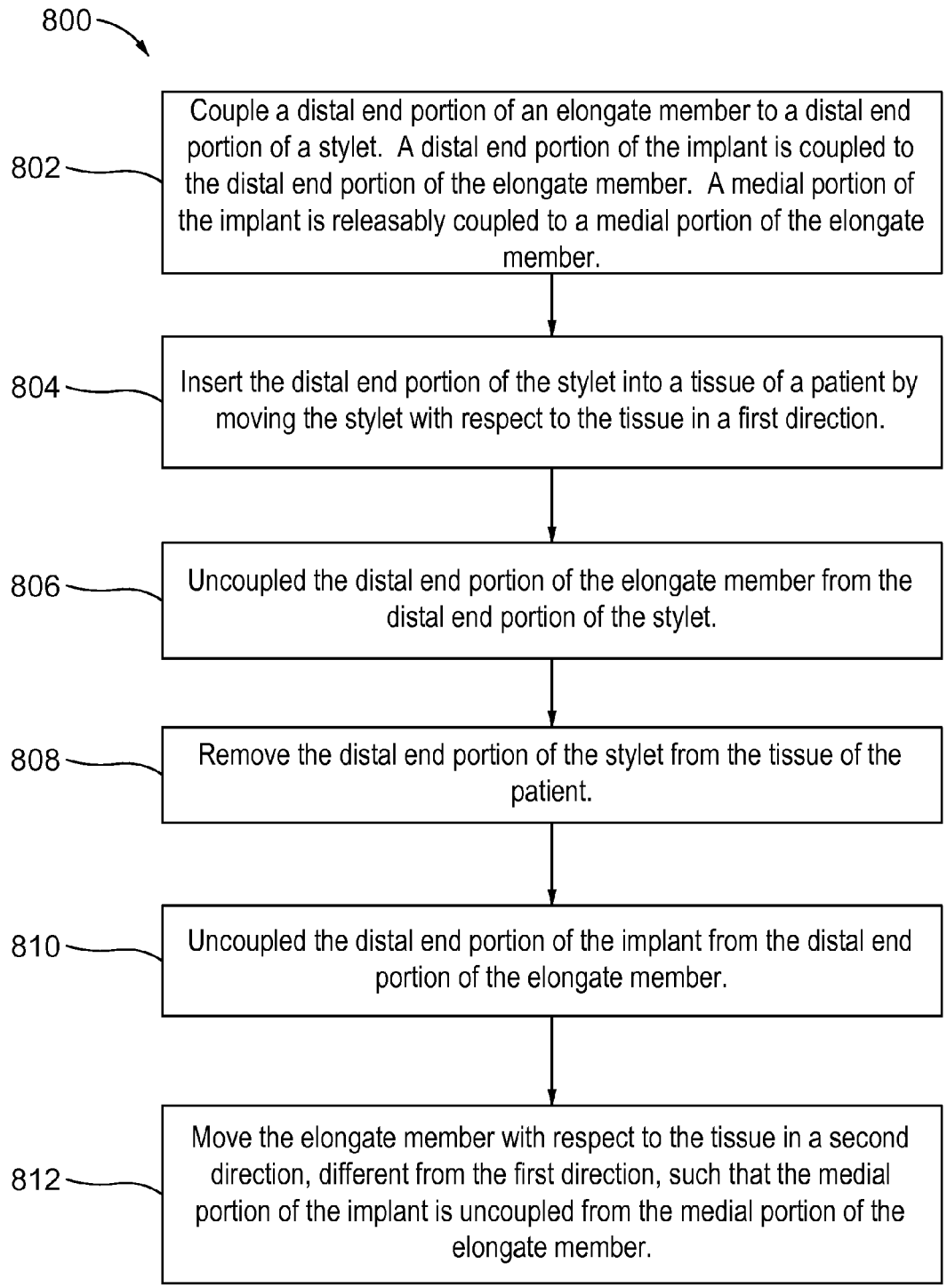
FIG. 18 is a flow chart illustrating a method of inserting an implant into a body of a patient, according to another embodiment.

FIG. 18 is a flow chart illustrating a method 800 of inserting an implant into a body of a patient, according to another embodiment. A distal end portion of an elongate member is coupled to a distal end portion of a stylet, at 802. A distal end portion of the implant is coupled to the distal end portion of the elongate member. A medial portion of the implant is releasably coupled to a medial portion of the elongate member. In other embodiments, a portion of the implant is also coupled to the proximal end portion of the elongate member.

The distal end portion of the stylet is inserted into a tissue of a patient by moving the stylet with respect to the tissue in a first direction, at 804. When moved in the first direction, retention members on the medial portion of the elongate member couple the medial portion of the implant to the elongate member and/or retain the medial portion of the implant against the elongate member.

The distal end portion of the elongate member is then uncoupled from the distal end portion of the stylet, at 806. The distal end portion of the stylet is removed from the tissue of the patient, at 808.

The distal end portion of the implant is uncoupled from the distal end portion of the elongate member, at 810. This can be done by removing the distal end portion of the elongate member from the elongate member (e.g., cutting the distal end portion of the elongate member off of the elongate member), removing the distal end portion of the implant from the implant (e.g., cutting the distal end portion of the implant off of the implant), unsnapping a snap-connector, unhooking a hook, removing the distal end portion of the elongate member from a lumen defined by the distal end portion of the implant and/or the like.

The elongate member is moved with respect to the tissue in a second direction, different from the first direction, such that the medial portion of the implant is uncoupled from the medial portion of the elongate member, at 812. When moved in the second direction, the retention members on the medial portion of the elongate member release the medial portion of the implant from the elongate member.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, in any of the above embodiments, an implant can be coupled to a distal end portion of an elongate member and/or a stylet and/or a proximal end portion of an elongate member and/or a stylet to secure the implant against the stylet during insertion into a body of a patient. In such embodiments, the medical practitioner can uncouple the implant from the end portions of the elongate member and/or stylet prior to removing the elongate member and/or stylet from the tissue of the patient.

In some embodiments, an insertion device includes a stylet having a proximal end portion, a distal end portion and a medial portion between the proximal end portion and the distal end portion. The distal end portion is configured to be releasably coupled to a first portion of an implant. The medial portion having at least one retention member configured to be releasably coupled to a second portion of the implant.

In some embodiments, the distal end portion is configured to be releasably coupled to the first portion of the implant via an intermediate member. In some embodiments, the medial portion of the stylet defines a center line that is curved. The at least one retention member of the medial portion is configured to releasably couple the second portion of the implant thereto such that the implant defines a center line that is parallel to the center line of the medial portion of the stylet.

In some embodiments, the at least one retention member is configured to be releasably coupled to the second portion of the implant when the stylet is moved in a first direction. The at least one retention member is configured to release the second portion of the implant when the stylet is moved in a second direction, different from the first direction.

In some embodiments, the at least one retention member is a hook. The second portion of the implant includes a mesh having a plurality of apertures. At least a portion of the hook is configured to be disposed within an aperture from the plurality of apertures when the medial portion of the stylet is releasably coupled to the second portion of the implant.

In some embodiments, the medial portion of the stylet has a width less than a width of the second portion of the implant. In some embodiments, the at least one retention member extends from the stylet a distance less than a thickness of the second portion of the implant such that the retention member does not contact tissue when the insertion device is inserted into a body of a patient and the second portion of the implant is coupled to the medial portion of the stylet.

In some embodiments, the at least one retention member is monolithically formed with the stylet. In some embodiments, the at least one retention member is releasably coupled to the medial portion of the stylet. In some embodiments, the distal end portion of the stylet is configured to be coupled to a tissue anchor on the first portion of the implant.

In some embodiments, an insertion device includes an elongate member having a retention member and at least one coupling mechanism. The at least one coupling mechanism is configured to releasably couple the elongate member to a stylet used to insert an implant into a tissue of a patient. The retention member is configured to releasably couple at least a portion of the implant to at least a portion of the elongate member.

In some embodiments, at least a portion of the implant is configured to be disposed between the stylet and the elongate member. In some embodiments, the retention member is configured to releasably couple at least a portion of the implant with at least a portion of the elongate member when the elongate member is moved through the tissue in a first direction. In such embodiments, the retention member is configured to release the implant when the elongate member is moved through the tissue in a second direction, different from the first direction.

In some embodiments, the retention member is a hook. The implant includes a mesh having a plurality of apertures. At least a portion of the hook is configured to be disposed within an aperture from the plurality of apertures when the elongate member is releasably coupled to the implant.

In some embodiments, the elongate member has a width less than a width of the implant. In some embodiments, the retention member has a height less than a thickness of the implant such that the retention member does not contact tissue when the elongate member is releasably coupled to the implant and inserted into a body of a patient.

In some embodiments, a distal end portion of the elongate member is coupled to a distal end portion of the implant. In some embodiments, the at least one coupling mechanism includes a dilator.

In some embodiments, a method of inserting an implant includes coupling a distal end portion of an elongate member to a distal end portion of a stylet. A distal end portion of the implant is coupled to the distal end portion of the elongate member. A medial end portion of the implant is releasably coupled to a medial portion of the elongate member. The distal end portion of the stylet is inserted into a tissue of a patient by moving the stylet with respect to the tissue in a first direction. The distal end portion of the elongate member is uncoupled from the distal end portion of the stylet. The distal end portion of the stylet is removed from the tissue of the patient. The distal end portion of the implant is uncoupled from the distal end portion of the elongate member. The elongate member is moved with respect to the tissue in a second direction, different from the first direction, such that the medial portion of the implant is uncoupled from the medial portion of the elongate member.

In some embodiments, the second direction is substantially opposite the first direction. In some embodiments, a proximal end portion of the elongate member is coupled to a proximal end portion of the stylet.

In some embodiments, a medical device includes a stylet, an elongate member and an implant. The elongate member has a distal end portion, a proximal end portion and a medial portion. The medial portion of the elongate member has a retention member. The elongate member is configured to be coupled to the stylet. The implant has a distal end portion, a proximal end portion and a medial portion. The distal end portion of the implant is coupled to the distal end portion of the elongate member. The medial portion of the implant is configured to be releasably coupled to the elongate member via the retention member.

In some embodiments, the elongate member is configured to be releasably coupled to the stylet. In some embodiments, the elongate member is monolithically formed with the stylet. In some embodiments, at least a portion of the implant is configured to be disposed between the stylet and the elongate member when the elongate member is coupled to the stylet.

In some embodiments, the retention member is a hook. The implant includes a mesh having a plurality of apertures. At least a portion of the hook is configured to be disposed within an aperture from the plurality of apertures when the elongate member is coupled to the implant. In some embodiments, the elongate member has a width less than a width of the implant. In some embodiments, the retention member has a height less than a thickness of the implant such that contact between tissue and the retention member is reduced when the elongate member is coupled to the implant and inserted into a body of a patient.

In some embodiments, a method includes inserting a distal end portion of a stylet through a tissue of a patient in a first direction. A first end portion of an elongate member is coupled to the distal end portion of the stylet. An implant is coupled to the elongate member. The distal end portion of the stylet, the elongate member and the implant are pulled through the tissue of the patient in a second direction, different from the first direction. The first end portion of the elongate member is uncoupled from the distal end portion of the stylet. The implant is uncoupled from the elongate member. The elongate member is pulled through the tissue of the patient in the first direction, such that the elongate member is removed from the tissue of the patient and the implant remains within the tissue of the patient.

In some embodiments, the second direction is substantially opposite the first direction. In some embodiments, the uncoupling the implant from the elongate member includes removing the first end portion of the elongate member from the elongate member and removing an end portion of the implant from the implant.

In some embodiments, a method includes inserting an implant assembly through a tissue of a patient in a first direction. The implant assembly includes a stylet, a first elongate member coupled to the stylet, a second elongate member coupled to the stylet and an implant coupled to the first elongate member and the second elongate member. The first elongate member and the second elongate member are uncoupled from the stylet. The stylet is removed from the tissue of the patient by moving the stylet in a second direction, different from the first direction. The implant is uncoupled from the first elongate member and the second elongate member. The first elongate member is removed from the tissue of the patient by moving the first elongate member in the second direction. The second elongate member is removed from the tissue of the patient by moving the second elongate member in the second direction.

In some embodiments, the second direction is substantially opposite the first direction. In some embodiments, the uncoupling the implant from the first elongate member includes removing an end portion of the first elongate member from the first elongate member and removing an end portion of the implant from the implant.

In some embodiments, the position of the implant is adjusted by moving the first elongate member in the first direction and the position of the implant is adjusted by moving the second elongate member in the second direction.

What is claimed is:

1. An insertion device, comprising:
a handle; and
a stylet having a proximal end portion coupled with the handle, a distal end portion, and a medial portion disposed between the proximal end portion and the distal end portion, the distal end portion being tapered and configured to pierce a tissue of a patient, the medial portion including an elongate member having an outer surface and a plurality of hook-shaped retention members extending perpendicular from the outer surface, the plurality of hook-shaped retention members of the elongate member being configured to receive a respective strand of a mesh implant so as to releasably couple the mesh implant with the stylet.

2. The insertion device of claim 1, wherein the distal end portion is configured to be releasably coupled with a portion of the mesh implant via an intermediate member.

3. The insertion device of claim 1, wherein the medial portion of the stylet defines a center line that is curved, the plurality of hook-shaped retention members of the elongate member being configured to releasably couple the mesh implant thereto such that the mesh implant defines a center line that is parallel to the center line of the medial portion of the stylet.

4. The insertion device of claim 1, wherein the plurality of hook-shaped retention members are configured to releasably couple the mesh implant to the stylet when the stylet is moved in a first direction, the plurality of hook-shaped retention members being configured to release the mesh implant from the stylet when the stylet is moved in a second direction, the second direction being different than the first direction.

5. The insertion device of claim 1, wherein a hook-shaped retention member of the plurality of hook-shaped retention members is configured to be disposed within a respective aperture of the mesh implant when the medial portion of the stylet is releasably coupled to the mesh implant.

6. The insertion device of claim 1, wherein the plurality of hook-shaped retention members are configured such that they do not contact tissue when the insertion device is inserted into a body of a patient and the mesh implant is releasably coupled to the medial portion of the stylet.

7. The insertion device of claim 1, wherein the elongate member is monolithically formed with the stylet.

8. The insertion device of claim 1, wherein the elongate member is releasably coupled to the medial portion of the stylet.

9. An insertion device, comprising:
an elongate member having:
a plurality of hook-shaped retention members disposed on, and extending perpendicularly from, a first side of the elongate member;
a first coupling mechanism disposed on a second side of the elongate member and disposed at a proximal end of the elongate member, the second side being opposite the first side; and
a second coupling mechanism disposed on the second side of the elongate member and disposed at a distal end of the elongate member,
the first coupling mechanism and the second coupling mechanism configured to releasably couple the elongate member to a stylet used to insert a mesh implant into a tissue of a patient, the plurality of hook-shaped retention members configured to releasably couple at least a portion of the mesh implant to at least a portion of the elongate member.

10. The insertion device of claim 9, wherein at least a portion of the implant is configured to be disposed between the stylet and the elongate member.

11. The insertion device of claim 9, wherein the plurality of hook-shaped retention members are configured to releasably couple the at least the portion of the implant with the at least the portion of the elongate member when the elongate member is moved into the tissue of the patient, the plurality of hook-shaped retention members being configured to release the implant when the elongate member is moved out of the tissue of the patient.

12. The insertion device of claim 9, wherein a hook-shaped retention member of the plurality of hook-shaped retention members is configured to be disposed within a respective aperture of the mesh implant when the elongate member is releasably coupled to the mesh implant.

13. The insertion device of claim 9, wherein a distal end portion of the elongate member is coupled to a distal end portion of the mesh implant.

14. The insertion device of claim 9, wherein the second coupling mechanism includes a dilator.

15. An insertion device, comprising:
a stylet having a proximal end portion, a distal end portion, and a medial portion between the proximal end portion and the distal end portion, the distal end portion configured to be releasably coupled to a first portion of an implant; and
an elongate member coupled with the stylet, the elongate member having a retention member fixedly disposed on an outer surface of the elongate member and at least one coupling mechanism, the at least one coupling mechanism being configured to releasably couple the elongate member to the stylet, the retention member of the elongate member being configured to releasably couple at least a portion of the implant to at least a portion of the elongate member.

16. The insertion device of claim 15, wherein the distal end portion of the stylet includes a dilator.

17. The insertion device of claim 15, wherein the distal end portion of the stylet is configured to be coupled to a tissue anchor affixed to the implant.

18. The insertion device of claim 15, wherein the retention member of the elongate member includes a curved portion of the elongate member.

* * * * *